US009717689B2

(12) United States Patent
Oberg et al.

(10) Patent No.: US 9,717,689 B2
(45) Date of Patent: Aug. 1, 2017

(54) METHOD OF DRUG FORMULATION BASED ON INCREASING THE AFFINITY OF CRYSTALLINE MICROPARTICLE SURFACES FOR ACTIVE AGENTS

(71) Applicant: MannKind Corporation, Valencia, CA (US)

(72) Inventors: Keith A. Oberg, Valencia, CA (US); Joseph Sulner, Paramus, NJ (US); Marshall L. Grant, Newtown, CT (US)

(73) Assignee: MannKind Corporation, Valencia, CA (US)

( * ) Notice: Subject to any disclaimer, the term of this patent is extended or adjusted under 35 U.S.C. 154(b) by 0 days.

(21) Appl. No.: 15/017,153

(22) Filed: Feb. 5, 2016

(65) Prior Publication Data
US 2016/0151287 A1 Jun. 2, 2016

Related U.S. Application Data

(60) Division of application No. 14/249,621, filed on Apr. 10, 2014, now Pat. No. 9,283,193, which is a continuation of application No. 12/830,557, filed on Jul. 6, 2010, now Pat. No. 8,729,019, which is a continuation of application No. 11/532,063, filed on Sep. 14, 2006, now Pat. No. 7,799,344.

(60) Provisional application No. 60/744,882, filed on Apr. 14, 2006, provisional application No. 60/717,524, filed on Sep. 14, 2005.

(51) Int. Cl.
| | | |
|---|---|---|
| A61K 38/13 | (2006.01) | |
| A61K 38/22 | (2006.01) | |
| A61K 38/25 | (2006.01) | |
| A61K 38/27 | (2006.01) | |
| A61K 38/28 | (2006.01) | |
| A61K 38/29 | (2006.01) | |
| A61K 9/16 | (2006.01) | |
| A61K 9/50 | (2006.01) | |
| A61K 9/00 | (2006.01) | |
| A61K 38/26 | (2006.01) | |

(52) U.S. Cl.
CPC .......... *A61K 9/1676* (2013.01); *A61K 9/0073* (2013.01); *A61K 9/167* (2013.01); *A61K 9/1611* (2013.01); *A61K 9/1617* (2013.01); *A61K 9/1623* (2013.01); *A61K 9/5052* (2013.01); *A61K 9/5089* (2013.01); *A61K 38/13* (2013.01); *A61K 38/22* (2013.01); *A61K 38/25* (2013.01); *A61K 38/26* (2013.01); *A61K 38/27* (2013.01); *A61K 38/28* (2013.01); *A61K 38/29* (2013.01)

(58) Field of Classification Search
CPC ........ A61K 38/13; A61K 38/22; A61K 38/25; A61K 38/27; A61K 38/28; A61K 38/29; A61K 9/1619; A61K 9/1623; A61K 9/167; A61K 9/1676; A61K 9/5052; A61K 9/5058; A61K 9/16
USPC ............................................ 514/5.9; 424/491
See application file for complete search history.

(56) References Cited

U.S. PATENT DOCUMENTS

| | | |
|---|---|---|
| 2,549,303 A | 4/1951 | Friden |
| 2,754,276 A | 7/1956 | Joseph et al. |
| D189,076 S | 10/1960 | Altman |
| 3,337,740 A | 8/1967 | Gray et al. |
| 3,407,203 A | 10/1968 | Buijle |
| 3,518,340 A | 6/1970 | Raper |
| 3,622,053 A | 11/1971 | Ryden |
| 3,669,113 A | 6/1972 | Altounyan et al. |
| 3,673,698 A | 7/1972 | Guerard |
| 3,823,816 A | 7/1974 | Controullis et al. |
| 3,823,843 A | 7/1974 | Stephens et al. |
| 3,856,142 A | 12/1974 | Vessalo |
| 3,873,651 A | 3/1975 | Mosley, Jr. et al. |
| 3,906,950 A | 9/1975 | Cocozza |
| 3,921,637 A | 11/1975 | Bennie et al. |
| 3,976,773 A | 8/1976 | Curran et al. |
| 3,980,074 A | 9/1976 | Watt et al. |
| 3,998,226 A | 12/1976 | Harris |
| 4,013,075 A | 3/1977 | Cocozza |
| 4,018,619 A | 4/1977 | Webster et al. |
| 4,022,749 A | 5/1977 | Kuechler |
| 4,040,536 A | 8/1977 | Schwarz |
| 4,047,525 A | 9/1977 | Kulessa et al. |
| 4,066,756 A | 1/1978 | Orr et al. |
| 4,078,128 A | 3/1978 | Hoyt et al. |
| 4,091,077 A | 5/1978 | Smith et al. |

(Continued)

FOREIGN PATENT DOCUMENTS

| | | |
|---|---|---|
| CA | 2536047 A1 | 3/2005 |
| CA | 2551182 C | 8/2010 |

(Continued)

OTHER PUBLICATIONS

Non-covalent interactions, Section 2.3, from UCDavis ChemWiki, pp. 1-4. Accessed Jul. 14, 2015.*

(Continued)

*Primary Examiner* — Julie Ha
(74) *Attorney, Agent, or Firm* — K&L Gates LLP; Louis C. Cullman; Robert W. Winn

(57) ABSTRACT

Methods are provided for coating crystalline microparticles with an active agent by altering the surface properties of the microparticles in order to facilitate favorable association on the microparticle by the active agent. Types of surface properties that are altered by the disclosed methods include electrostatic properties, hydrophobic properties, and hydrogen bonding properties.

20 Claims, 7 Drawing Sheets

(56) References Cited

U.S. PATENT DOCUMENTS

Figure 1:
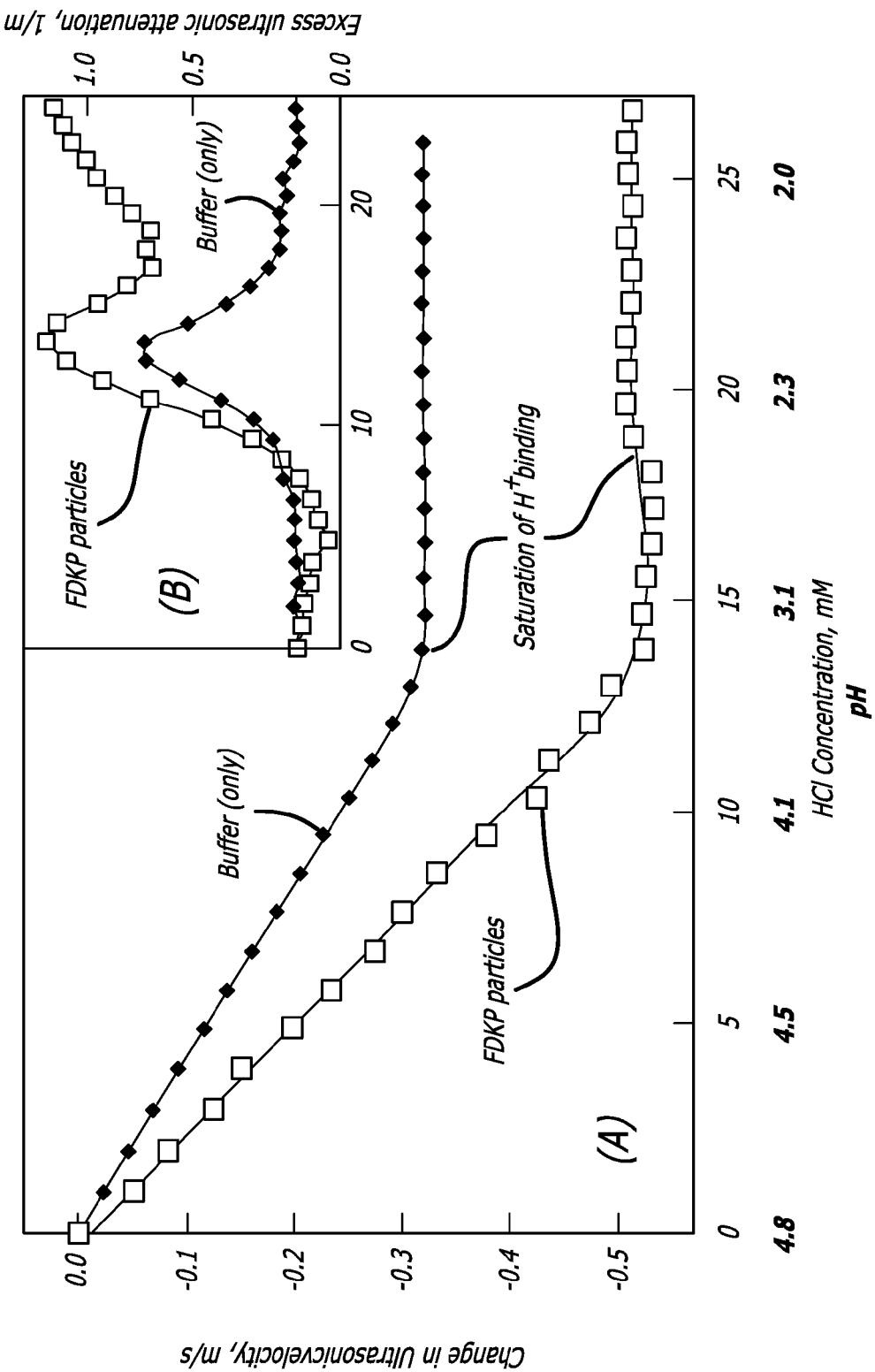

| Patent No. | Date | Inventor |
|---|---|---|
| 4,098,273 A | 7/1978 | Glenn |
| 4,102,953 A | 7/1978 | Johnson et al. |
| 4,110,240 A | 8/1978 | Leo et al. |
| 4,148,308 A | 4/1979 | Sayer |
| 4,153,689 A | 5/1979 | Hirai |
| D252,707 S | 8/1979 | Besnard |
| 4,168,002 A | 9/1979 | Crosby |
| 4,171,000 A | 10/1979 | Uhle |
| 4,175,556 A | 11/1979 | Freezer |
| 4,187,129 A | 2/1980 | Bost et al. |
| 4,196,196 A | 4/1980 | Tiholiz |
| 4,206,758 A | 6/1980 | Hallworth et al. |
| 4,210,140 A | 7/1980 | James et al. |
| 4,211,769 A | 7/1980 | Okada |
| 4,268,460 A | 5/1981 | Boiarski et al. |
| 4,272,398 A | 6/1981 | Jaffe |
| 4,275,820 A | 6/1981 | LeBlond |
| 4,289,759 A | 9/1981 | Heavener |
| 4,294,829 A | 10/1981 | Suzuki |
| 4,300,546 A | 11/1981 | Kruber |
| 4,356,167 A | 10/1982 | Kelly |
| D269,463 S | 6/1983 | Young |
| 4,407,525 A | 10/1983 | Hoppe |
| 4,456,007 A | 6/1984 | Nakao et al. |
| 4,483,922 A | 11/1984 | Carpenter |
| D276,654 S | 12/1984 | Snellman-Wasenius et al. |
| 4,487,327 A | 12/1984 | Grayson |
| 4,524,769 A | 6/1985 | Wetterlin |
| 4,526,804 A | 7/1985 | Escallon |
| 4,534,345 A | 8/1985 | Wetterlin |
| D282,209 S | 1/1986 | Newell et al. |
| 4,581,020 A | 4/1986 | Mittleman |
| 4,592,348 A | 6/1986 | Waters, IV et al. |
| 4,613,500 A | 9/1986 | Suzuki |
| 4,615,817 A | 10/1986 | McCoy |
| 4,624,861 A | 11/1986 | Yale et al. |
| 4,637,996 A | 1/1987 | Konishi |
| D288,852 S | 3/1987 | Miyoshi |
| 4,659,696 A | 4/1987 | Hirai et al. |
| 4,668,218 A | 5/1987 | Virtanen |
| 4,681,752 A | 7/1987 | Melillo |
| D295,321 S | 4/1988 | Hallworth |
| 4,757,066 A | 7/1988 | Shiokari et al. |
| 4,792,451 A | 12/1988 | Kim |
| 4,811,731 A | 3/1989 | Newell et al. |
| D301,273 S | 5/1989 | Leonard |
| 4,835,312 A | 5/1989 | Itoh et al. |
| 4,841,964 A | 6/1989 | Hurka et al. |
| 4,847,091 A | 7/1989 | Illum |
| 4,849,227 A | 7/1989 | Cho |
| 4,861,627 A | 8/1989 | Mathiowitz |
| 4,866,051 A | 9/1989 | Hunt et al. |
| 4,873,087 A | 10/1989 | Morishita et al. |
| 4,887,722 A | 12/1989 | Greenward, Sr. |
| 4,900,730 A | 2/1990 | Miyauchi |
| 4,907,583 A | 3/1990 | Wetterlin et al. |
| 4,925,673 A | 5/1990 | Steiner |
| 4,926,852 A | 5/1990 | Zoltan et al. |
| 4,927,555 A | 5/1990 | Colarusso, Jr. |
| 4,927,928 A | 5/1990 | Shroot et al. |
| 4,946,828 A | 8/1990 | Markussen |
| 4,981,295 A | 1/1991 | Belman et al. |
| 4,981,625 A | 1/1991 | Rhim et al. |
| 4,983,402 A | 1/1991 | Steiner et al. |
| 4,984,158 A | 1/1991 | Hillsman |
| 4,991,605 A | 2/1991 | Keritsis |
| 4,998,624 A | 3/1991 | Capes et al. |
| 5,006,343 A | 4/1991 | Benson |
| D316,902 S | 5/1991 | Hoelfing |
| 5,017,383 A | 5/1991 | Ozawa et al. |
| 5,019,400 A | 5/1991 | Gombotz et al. |
| 5,021,376 A | 6/1991 | Nienburg et al. |
| 5,027,806 A | 7/1991 | Zoltan et al. |
| 5,042,975 A | 8/1991 | Chien |
| D321,570 S | 11/1991 | Blasdell et al. |
| 5,067,500 A | 11/1991 | Keritsis |
| 5,069,204 A | 12/1991 | Smith et al. |
| 5,074,418 A | 12/1991 | Buan et al. |
| 5,075,027 A | 12/1991 | Dixit et al. |
| 5,098,590 A | 3/1992 | Dixit et al. |
| 5,105,291 A | 4/1992 | Matsumoto et al. |
| D326,517 S | 5/1992 | Funai et al. |
| 5,110,007 A | 5/1992 | Law et al. |
| 5,110,823 A | 5/1992 | Hamaguchi et al. |
| 5,118,666 A | 6/1992 | Habener |
| 5,120,712 A | 6/1992 | Habener |
| 5,124,291 A | 6/1992 | Bremer et al. |
| 5,131,539 A | 7/1992 | Karita et al. |
| 5,139,878 A | 8/1992 | Kim |
| 5,145,684 A | 9/1992 | Liversidge et al. |
| 5,152,284 A | 10/1992 | Valentini et al. |
| D331,106 S | 11/1992 | Fuchs |
| 5,167,506 A | 12/1992 | Kilis et al. |
| 5,170,801 A | 12/1992 | Casper et al. |
| 5,188,837 A | 2/1993 | Domb |
| 5,196,049 A | 3/1993 | Coombs et al. |
| 5,201,308 A | 4/1993 | Newhouse |
| 5,203,768 A | 4/1993 | Haak et al. |
| 5,204,108 A | 4/1993 | Illum |
| 5,208,998 A | 5/1993 | Dyler, Jr. |
| 5,215,739 A | 6/1993 | Kamishita et al. |
| D337,636 S | 7/1993 | Kocinski |
| D338,062 S | 8/1993 | Yair |
| D338,268 S | 8/1993 | Kobayashi et al. |
| 5,239,992 A | 8/1993 | Bougamont et al. |
| 5,244,653 A | 9/1993 | Berke et al. |
| 5,250,287 A | 10/1993 | Cocozza |
| D340,975 S | 11/1993 | Sladek |
| 5,260,306 A | 11/1993 | Boardman et al. |
| 5,270,305 A | 12/1993 | Palmer |
| 5,287,850 A | 2/1994 | Haber et al. |
| D344,796 S | 3/1994 | Sochon et al. |
| D344,797 S | 3/1994 | Sochon et al. |
| D345,013 S | 3/1994 | Huck et al. |
| 5,301,666 A | 4/1994 | Lerk et al. |
| 5,306,453 A | 4/1994 | Shulman |
| D347,057 S | 5/1994 | Yair |
| D348,100 S | 6/1994 | Clarke |
| 5,320,094 A | 6/1994 | Laube et al. |
| D348,928 S | 7/1994 | Ashley et al. |
| D348,929 S | 7/1994 | Paton |
| 5,327,883 A | 7/1994 | Williams et al. |
| 5,328,464 A | 7/1994 | Kriesel et al. |
| 5,331,953 A | 7/1994 | Andersson et al. |
| 5,333,106 A | 7/1994 | Lanpher et al. |
| D349,572 S | 8/1994 | Jagnandan et al. |
| D350,193 S | 8/1994 | Huck et al. |
| 5,337,740 A | 8/1994 | Armstrong et al. |
| D350,602 S | 9/1994 | Hobbs et al. |
| D350,821 S | 9/1994 | Wright et al. |
| 5,351,683 A | 10/1994 | Chiesi et al. |
| 5,352,461 A | 10/1994 | Feldstein et al. |
| 5,354,562 A | 10/1994 | Platz |
| 5,358,734 A | 10/1994 | Lenox et al. |
| D352,107 S | 11/1994 | Meier et al. |
| 5,360,614 A | 11/1994 | Fox et al. |
| 5,363,842 A | 11/1994 | Mishelevich et al. |
| 5,364,838 A | 11/1994 | Rubsamen |
| 5,372,128 A | 12/1994 | Haber et al. |
| D355,029 S | 1/1995 | Kinneir et al. |
| 5,385,904 A | 1/1995 | Andersson et al. |
| 5,394,868 A | 3/1995 | Ambrosio et al. |
| 5,401,516 A | 3/1995 | Milstein et al. |
| D357,603 S | 4/1995 | Wolff |
| 5,404,871 A | 4/1995 | Goodman et al. |
| D358,880 S | 5/1995 | Mulhauser et al. |
| 5,413,804 A | 5/1995 | Rhodes |
| 5,415,162 A | 5/1995 | Casper et al. |
| D359,153 S | 6/1995 | Viggiano |
| D359,555 S | 6/1995 | Funai et al. |
| 5,424,286 A | 6/1995 | Eng |
| 5,437,271 A | 8/1995 | Hodson et al. |
| 5,443,841 A | 8/1995 | Milstein et al. |
| D362,500 S | 9/1995 | Cook et al. |

(56) References Cited

U.S. PATENT DOCUMENTS

| | | |
|---|---|---|
| 5,447,150 A | 9/1995 | Bacon |
| 5,447,151 A | 9/1995 | Bruna et al. |
| 5,447,728 A | 9/1995 | Milstein et al. |
| 5,451,410 A | 9/1995 | Milstein et al. |
| D363,775 S | 10/1995 | Hobbs |
| 5,454,871 A | 10/1995 | Liaw et al. |
| 5,455,335 A | 10/1995 | Kahne et al. |
| 5,458,135 A | 10/1995 | Patton et al. |
| 5,469,750 A | 11/1995 | Lloyd et al. |
| 5,469,971 A | 11/1995 | Chilton et al. |
| 5,476,093 A | 12/1995 | Laniken |
| 5,477,285 A | 12/1995 | Riddle et al. |
| D365,876 S | 1/1996 | Chawla |
| 5,482,032 A | 1/1996 | Smith et al. |
| 5,482,927 A | 1/1996 | Maniar et al. |
| 5,483,954 A | 1/1996 | Mecikalski |
| 5,484,606 A | 1/1996 | Dhaber et al. |
| 5,487,378 A | 1/1996 | Robertson et al. |
| 5,492,112 A | 2/1996 | Mecikalski et al. |
| D368,364 S | 4/1996 | Reitano et al. |
| 5,503,144 A | 4/1996 | Bacon |
| 5,503,852 A | 4/1996 | Steiner et al. |
| 5,505,194 A | 4/1996 | Adjei et al. |
| 5,506,203 A | 4/1996 | Backstrom et al. |
| D370,255 S | 5/1996 | Yamamoto et al. |
| 5,514,646 A | 5/1996 | Chance et al. |
| 5,518,998 A | 5/1996 | Backstrom et al. |
| 5,524,613 A | 6/1996 | Haber et al. |
| 5,532,461 A | 7/1996 | Crummenauer et al. |
| 5,533,502 A | 7/1996 | Piper |
| 5,533,505 A | 7/1996 | Kallstrand et al. |
| 5,541,155 A | 7/1996 | Leone-Bay |
| 5,542,411 A | 8/1996 | Rex |
| 5,542,539 A | 8/1996 | Early |
| 5,545,618 A | 8/1996 | Buckley et al. |
| 5,547,929 A | 8/1996 | Anderson, Jr. et al. |
| 5,562,909 A | 10/1996 | Allcock et al. |
| 5,562,918 A | 10/1996 | Stimpson |
| 5,568,884 A | 10/1996 | Bruna |
| 5,570,810 A | 11/1996 | Lambelet, Jr. et al. |
| 5,571,795 A | 11/1996 | Kahne et al. |
| 5,574,008 A | 11/1996 | Johnson et al. |
| 5,577,497 A | 11/1996 | Mecikalski et al. |
| 5,578,323 A | 11/1996 | Milstein et al. |
| 5,584,417 A | 12/1996 | Graf et al. |
| D377,215 S | 1/1997 | Rand |
| D377,686 S | 1/1997 | Waldeck et al. |
| 5,595,175 A | 1/1997 | Malcher et al. |
| 5,596,701 A | 1/1997 | Augusteijn et al. |
| D377,861 S | 2/1997 | Jacober |
| 5,598,835 A | 2/1997 | von Schrader |
| 5,601,846 A | 2/1997 | Milstein et al. |
| 5,610,271 A | 3/1997 | Dooley et al. |
| 5,614,492 A | 3/1997 | Habener |
| 5,615,670 A | 4/1997 | Rhodes et al. |
| 5,617,844 A | 4/1997 | King |
| 5,619,984 A | 4/1997 | Hodson et al. |
| 5,622,164 A | 4/1997 | Kilis et al. |
| 5,622,166 A | 4/1997 | Eisele et al. |
| 5,623,724 A | 4/1997 | Gurkovich et al. |
| 5,623,920 A | 4/1997 | Bryant |
| D379,506 S | 5/1997 | Maher |
| 5,629,020 A | 5/1997 | Leone-Bay |
| 5,631,224 A | 5/1997 | Efendic et al. |
| 5,632,971 A | 5/1997 | Yang |
| 5,634,900 A | 6/1997 | Makino et al. |
| 5,639,441 A | 6/1997 | Sievers et al. |
| 5,641,861 A | 6/1997 | Dooley et al. |
| D381,416 S | 7/1997 | Hansson et al. |
| 5,642,727 A | 7/1997 | Datta et al. |
| 5,642,728 A | 7/1997 | Andersson et al. |
| 5,643,957 A | 7/1997 | Leone-Bay et al. |
| 5,645,051 A | 7/1997 | Schultz |
| 5,651,359 A | 7/1997 | Bougamont et al. |
| 5,653,961 A | 8/1997 | McNally et al. |
| 5,655,516 A | 8/1997 | Goodman et al. |
| 5,655,523 A | 8/1997 | Hodson et al. |
| 5,657,748 A | 8/1997 | Braithwaite |
| 5,658,878 A | 8/1997 | Backstrom et al. |
| 5,660,169 A | 8/1997 | Kallstrand et al. |
| 5,672,581 A | 9/1997 | Rubsamen et al. |
| 5,673,686 A | 10/1997 | Villax et al. |
| 5,679,377 A | 10/1997 | Bernstein et al. |
| 5,687,710 A | 11/1997 | Ambrosio et al. |
| 5,690,910 A | 11/1997 | Ahmed et al. |
| 5,693,338 A | 12/1997 | Milstein |
| 5,699,789 A | 12/1997 | Hendricks |
| D389,238 S | 1/1998 | Kirk, III et al. |
| D389,570 S | 1/1998 | Savolainen |
| 5,705,483 A | 1/1998 | Galloway et al. |
| D390,651 S | 2/1998 | Smith et al. |
| D390,653 S | 2/1998 | Blasdell et al. |
| 5,714,007 A | 2/1998 | Pletcher et al. |
| 5,714,167 A | 2/1998 | Milstein et al. |
| 5,727,333 A | 3/1998 | Folan |
| 5,727,546 A | 3/1998 | Clarke et al. |
| 5,740,793 A | 4/1998 | Hodson et al. |
| 5,740,794 A | 4/1998 | Smith et al. |
| 5,746,197 A | 5/1998 | Williams |
| 5,746,227 A | 5/1998 | Rose et al. |
| 5,747,445 A | 5/1998 | Backstrom et al. |
| 5,752,505 A | 5/1998 | Ohki et al. |
| 5,755,218 A | 5/1998 | Johansson et al. |
| D395,147 S | 6/1998 | Vidgren et al. |
| D395,499 S | 6/1998 | Eisele et al. |
| 5,758,638 A | 6/1998 | Kreamer |
| 5,763,396 A | 6/1998 | Weiner et al. |
| 5,766,620 A | 6/1998 | Heiber et al. |
| 5,766,633 A | 6/1998 | Milstein et al. |
| 5,769,073 A | 6/1998 | Eason et al. |
| 5,772,085 A | 6/1998 | Bryant et al. |
| RE35,862 E | 7/1998 | Steiner et al. |
| 5,775,320 A | 7/1998 | Patton et al. |
| 5,785,049 A | 7/1998 | Smith et al. |
| 5,785,989 A | 7/1998 | Stanley et al. |
| D397,435 S | 8/1998 | Naumann |
| 5,792,451 A | 8/1998 | Sarubbi et al. |
| 5,794,613 A | 8/1998 | Piskorski |
| 5,797,391 A | 8/1998 | Cook et al. |
| D398,992 S | 9/1998 | Feret |
| 5,799,821 A | 9/1998 | Lambelet, Jr. et al. |
| 5,807,315 A | 9/1998 | Va Antwerp et al. |
| 5,809,997 A | 9/1998 | Wolf |
| 5,811,127 A | 9/1998 | Milstein et al. |
| 5,813,397 A | 9/1998 | Goodman et al. |
| 5,817,343 A | 10/1998 | Burke |
| 5,824,345 A | 10/1998 | Milstein et al. |
| 5,839,429 A | 11/1998 | Marnfeldt et al. |
| 5,840,279 A | 11/1998 | Narodylo et al. |
| 5,840,340 A | 11/1998 | Milstein et al. |
| 5,846,447 A | 12/1998 | Beatty |
| 5,848,589 A | 12/1998 | Welnetz |
| 5,849,322 A | 12/1998 | Ebert et al. |
| 5,857,457 A | 1/1999 | Hyppola |
| 5,858,099 A | 1/1999 | Sun et al. |
| 5,865,012 A | 2/1999 | Hansson et al. |
| 5,868,774 A | 2/1999 | Reil |
| 5,874,064 A | 2/1999 | Edwards et al. |
| 5,875,776 A | 3/1999 | Vaghefi |
| 5,877,174 A | 3/1999 | Ono et al. |
| 5,881,719 A | 3/1999 | Gottenauer et al. |
| 5,881,721 A | 3/1999 | Bunce et al. |
| 5,884,620 A | 3/1999 | Gonda et al. |
| 5,888,477 A | 3/1999 | Gonda et al. |
| 5,896,855 A | 4/1999 | Hobbs et al. |
| 5,901,703 A | 5/1999 | Ohki et al. |
| 5,904,139 A | 5/1999 | Hauser |
| D410,541 S | 6/1999 | Moulin |
| D411,005 S | 6/1999 | Coe |
| 5,908,639 A | 6/1999 | Simpkin et al. |
| 5,912,011 A | 6/1999 | Makino et al. |
| 5,918,594 A | 7/1999 | Asking et al. |
| 5,919,897 A | 7/1999 | Dooley et al. |
| 5,921,237 A | 7/1999 | Eisele et al. |

(56) References Cited

U.S. PATENT DOCUMENTS

| | | |
|---|---|---|
| 5,922,253 A | 7/1999 | Herbert et al. |
| 5,924,419 A | 7/1999 | Kotliar |
| 5,929,027 A | 7/1999 | Takama et al. |
| D412,572 S | 8/1999 | Gray |
| D412,744 S | 8/1999 | Braithwaite |
| D412,978 S | 8/1999 | Cameron |
| D412,979 S | 8/1999 | Weinstein et al. |
| 5,934,273 A | 8/1999 | Andersson et al. |
| 5,942,242 A | 8/1999 | Mizushima et al. |
| 5,948,749 A | 9/1999 | Igarashi et al. |
| 5,952,008 A | 9/1999 | Backstrom et al. |
| 5,954,047 A | 9/1999 | Armer et al. |
| 5,965,701 A | 10/1999 | Junien |
| 5,971,951 A | 10/1999 | Ruskewicz |
| D416,085 S | 11/1999 | Forssell et al. |
| D416,621 S | 11/1999 | Forssell et al. |
| D416,998 S | 11/1999 | Hodson et al. |
| D417,271 S | 11/1999 | Denyer et al. |
| 5,975,347 A | 11/1999 | Lambelet, Jr. et al. |
| 5,976,569 A | 11/1999 | Milstein |
| 5,976,574 A | 11/1999 | Gordon |
| 5,977,071 A | 11/1999 | Galloway et al. |
| 5,980,865 A | 11/1999 | Ahmed et al. |
| 5,981,488 A | 11/1999 | Hoffmann |
| 5,983,893 A | 11/1999 | Wetterlin |
| 5,985,248 A | 11/1999 | Gordon et al. |
| 5,985,309 A | 11/1999 | Edwards et al. |
| 5,990,077 A | 11/1999 | Drucker |
| D417,732 S | 12/1999 | Dagsland et al. |
| D417,912 S | 12/1999 | Dagsland et al. |
| 5,996,577 A | 12/1999 | Ohki et al. |
| 5,997,848 A | 12/1999 | Patton et al. |
| 6,001,336 A | 12/1999 | Gordon |
| 6,006,747 A | 12/1999 | Eisele et al. |
| 6,006,753 A | 12/1999 | Efendic |
| D418,600 S | 1/2000 | Haerle |
| D420,736 S | 2/2000 | Moulin |
| 6,026,809 A | 2/2000 | Abrams et al. |
| 6,029,663 A | 2/2000 | Eisele et al. |
| D421,800 S | 3/2000 | Doat |
| 6,039,208 A | 3/2000 | Lambelet et al. |
| 6,043,214 A | 3/2000 | Jensen et al. |
| 6,045,828 A | 4/2000 | Bystrom et al. |
| 6,051,256 A | 4/2000 | Platz et al. |
| 6,051,551 A | 4/2000 | Hughes et al. |
| 6,055,980 A | 5/2000 | Mecikalski et al. |
| 6,056,169 A | 5/2000 | Bruna et al. |
| 6,060,069 A | 5/2000 | Hill et al. |
| 6,063,910 A | 5/2000 | Debenedetti et al. |
| 6,071,497 A | 6/2000 | Steiner et al. |
| 6,073,629 A | 6/2000 | Hardy et al. |
| 6,076,521 A | 6/2000 | Lindahl et al. |
| 6,077,543 A | 6/2000 | Gordon et al. |
| 6,080,762 A | 6/2000 | Allen et al. |
| D428,486 S | 7/2000 | Schuckmann |
| 6,085,745 A | 7/2000 | Levander et al. |
| 6,087,334 A | 7/2000 | Beeley et al. |
| 6,087,351 A | 7/2000 | Nyce |
| 6,089,228 A | 7/2000 | Smith et al. |
| 6,095,136 A | 8/2000 | Virtanen |
| 6,098,618 A | 8/2000 | Jennings et al. |
| 6,098,619 A | 8/2000 | Britto et al. |
| 6,099,517 A | 8/2000 | Daugherty |
| 6,102,035 A | 8/2000 | Asking et al. |
| 6,105,571 A | 8/2000 | Coffee |
| 6,105,574 A | 8/2000 | Jahnsson |
| 6,109,261 A | 8/2000 | Clarke et al. |
| 6,109,481 A | 8/2000 | Alexander et al. |
| 6,116,237 A | 9/2000 | Schultz |
| 6,116,238 A | 9/2000 | Jackson et al. |
| 6,116,239 A | 9/2000 | Volgyesi |
| 6,119,684 A | 9/2000 | Nohl et al. |
| 6,119,688 A | 9/2000 | Whaley et al. |
| 6,131,567 A | 10/2000 | Gonda et al. |
| 6,132,766 A | 10/2000 | Sankaram et al. |
| 6,133,235 A | 10/2000 | Galloway et al. |
| 6,142,145 A | 11/2000 | Dagsland |
| 6,152,130 A | 11/2000 | Abrams |
| 6,153,613 A | 11/2000 | Ono et al. |
| 6,155,423 A | 12/2000 | Katzner et al. |
| 6,156,114 A | 12/2000 | Bell et al. |
| 6,158,431 A | 12/2000 | Poole |
| 6,159,360 A | 12/2000 | Gerteis et al. |
| RE37,053 E | 2/2001 | Hanes et al. |
| 6,182,655 B1 | 2/2001 | Keller et al. |
| 6,187,291 B1 | 2/2001 | Weinstein et al. |
| 6,191,102 B1 | 2/2001 | DiMarchi et al. |
| 6,192,876 B1 | 2/2001 | Denyer et al. |
| 6,193,844 B1 | 2/2001 | McLaughlin et al. |
| 6,193,957 B1 | 2/2001 | Ahmed |
| D438,612 S | 3/2001 | Suh |
| D439,325 S | 3/2001 | Frost |
| D439,656 S | 3/2001 | Andersson et al. |
| 6,198,847 B1 | 3/2001 | Washizawa |
| D441,446 S | 5/2001 | Dagsland et al. |
| D441,859 S | 5/2001 | Pera |
| D442,685 S | 5/2001 | Sladek |
| 6,235,725 B1 | 5/2001 | Ahmed |
| D444,226 S | 6/2001 | Geert-Jensen et al. |
| 6,250,300 B1 | 6/2001 | Andersson et al. |
| 6,254,854 B1 | 7/2001 | Edwards et al. |
| 6,257,232 B1 | 7/2001 | Andersson et al. |
| 6,258,816 B1 | 7/2001 | Singh et al. |
| 6,263,871 B1 | 7/2001 | Brown et al. |
| 6,269,952 B1 | 8/2001 | Watt et al. |
| 6,273,084 B1 | 8/2001 | Frid |
| 6,273,085 B1 | 8/2001 | Eisele et al. |
| 6,273,086 B1 | 8/2001 | Ohki et al. |
| 6,277,819 B1 | 8/2001 | Efendic |
| 6,279,511 B1 | 8/2001 | Loughnane |
| D448,076 S | 9/2001 | von Schuckmann |
| 6,286,506 B1 | 9/2001 | MacAndrew et al. |
| 6,286,507 B1 | 9/2001 | Jahnsson |
| 6,294,204 B1 | 9/2001 | Rossling et al. |
| D449,684 S | 10/2001 | Christup et al. |
| 6,298,846 B1 | 10/2001 | Ohki et al. |
| 6,298,847 B1 | 10/2001 | Datta et al. |
| D450,117 S | 11/2001 | Braithwaite et al. |
| D451,597 S | 12/2001 | Suh |
| 6,328,034 B1 | 12/2001 | Eisele et al. |
| 6,331,318 B1 | 12/2001 | Milstein |
| D452,910 S | 1/2002 | Braithwaite et al. |
| 6,335,316 B1 | 1/2002 | Hughes et al. |
| D453,264 S | 2/2002 | Acevedo, Jr. |
| 6,347,629 B1 | 2/2002 | Braithwaite |
| 6,348,447 B1 | 2/2002 | Hellstrom et al. |
| 6,357,442 B1 | 3/2002 | Casper et al. |
| 6,358,058 B1 | 3/2002 | Strupat et al. |
| 6,358,924 B1 | 3/2002 | Hoffmann |
| 6,360,743 B1 | 3/2002 | Andersson et al. |
| 6,360,929 B1 | 3/2002 | McCarthy |
| D455,208 S | 4/2002 | Bacon et al. |
| 6,363,932 B1 | 4/2002 | Forchione et al. |
| 6,365,190 B1 | 4/2002 | Gordon et al. |
| 6,372,258 B1 | 4/2002 | Platz et al. |
| 6,375,975 B1 | 4/2002 | Modi |
| 6,380,357 B2 | 4/2002 | Hermeling et al. |
| 6,386,195 B1 | 5/2002 | Coffee |
| 6,388,053 B1 | 5/2002 | Galloway et al. |
| 6,394,085 B1 | 5/2002 | Hardy et al. |
| 6,395,300 B1 | 5/2002 | Straub et al. |
| 6,395,744 B1 | 5/2002 | Adams et al. |
| 6,395,774 B1 | 5/2002 | Milstein |
| 6,410,513 B1 | 6/2002 | Galloway et al. |
| D460,173 S | 7/2002 | Harrison et al. |
| 6,415,784 B1 | 7/2002 | Christrup et al. |
| 6,418,926 B1 | 7/2002 | Chawla |
| 6,423,344 B1 | 7/2002 | Platz et al. |
| D461,239 S | 8/2002 | Cassidy |
| 6,427,688 B1 | 8/2002 | Ligotke et al. |
| 6,428,771 B1 | 8/2002 | Steiner et al. |
| 6,428,805 B1 | 8/2002 | Dohi et al. |
| 6,432,383 B1 | 8/2002 | Modi |
| 6,436,443 B2 | 8/2002 | Edwards et al. |

(56) References Cited

U.S. PATENT DOCUMENTS

| | | |
|---|---|---|
| 6,439,227 B1 | 8/2002 | Myrman et al. |
| 6,440,463 B1 | 8/2002 | Feldstein et al. |
| 6,441,172 B1 | 8/2002 | Nefzi et al. |
| D463,544 S | 9/2002 | Engelbreth et al. |
| 6,443,143 B1 | 9/2002 | Ishida et al. |
| 6,444,226 B1 | 9/2002 | Steiner et al. |
| 6,446,626 B1 | 9/2002 | Virtanen |
| 6,446,627 B1 | 9/2002 | Bowman et al. |
| 6,447,750 B1 | 9/2002 | Cutie et al. |
| 6,447,751 B1 | 9/2002 | Weinstein et al. |
| 6,447,753 B2 | 9/2002 | Edwards et al. |
| 6,451,337 B1 | 9/2002 | Smith et al. |
| 6,457,470 B1 | 10/2002 | Coffee |
| 6,468,507 B1 | 10/2002 | Cutie et al. |
| 6,470,884 B2 | 10/2002 | Horlin |
| 6,479,049 B1 | 11/2002 | Platz et al. |
| 6,484,715 B1 | 11/2002 | Ritsche et al. |
| 6,484,717 B1 | 11/2002 | Dagsland et al. |
| D469,527 S | 1/2003 | Keller et al. |
| 6,503,480 B1 | 1/2003 | Edwards et al. |
| 6,509,006 B1 | 1/2003 | Platz et al. |
| 6,509,313 B1 | 1/2003 | Smith |
| D469,866 S | 2/2003 | Albulet et al. |
| 6,514,482 B1 | 2/2003 | Bartus et al. |
| 6,518,239 B1 | 2/2003 | Kuo et al. |
| 6,523,536 B2 | 2/2003 | Fugelsang et al. |
| D471,273 S | 3/2003 | Albulet et al. |
| 6,528,096 B1 | 3/2003 | Musa et al. |
| 6,532,437 B1 | 3/2003 | Clardy et al. |
| 6,536,427 B2 | 3/2003 | Davies et al. |
| D473,298 S | 4/2003 | Bowman et al. |
| D473,640 S | 4/2003 | Cuffaro et al. |
| 6,540,672 B1 | 4/2003 | Simonsen et al. |
| 6,540,982 B1 | 4/2003 | Adjei et al. |
| 6,540,983 B1 | 4/2003 | Adjei et al. |
| 6,543,448 B1 | 4/2003 | Smith et al. |
| 6,546,929 B2 | 4/2003 | Burr et al. |
| 6,555,127 B2 | 4/2003 | Steiner |
| 6,555,521 B2 | 4/2003 | Hermeling et al. |
| D474,536 S | 5/2003 | Albulet et al. |
| D475,133 S | 5/2003 | McLuckie |
| 6,557,549 B2 | 5/2003 | Schmidt et al. |
| 6,561,186 B2 | 5/2003 | Casper et al. |
| 6,567,686 B2 | 5/2003 | Sexton |
| 6,568,390 B2 | 5/2003 | Nichols et al. |
| 6,569,406 B2 | 5/2003 | Stevenson et al. |
| 6,571,793 B1 | 6/2003 | Nilsson et al. |
| 6,572,893 B2 | 6/2003 | Gordon et al. |
| 6,575,160 B1 | 6/2003 | Volgyesi |
| 6,575,162 B1 | 6/2003 | Rand |
| 6,578,571 B1 | 6/2003 | Watt |
| 6,582,728 B1 | 6/2003 | Platz et al. |
| 6,583,111 B1 | 6/2003 | DiMarchi |
| D477,665 S | 7/2003 | Myrman et al. |
| 6,589,560 B2 | 7/2003 | Foster et al. |
| 6,591,832 B1 | 7/2003 | DeJonge |
| 6,592,904 B2 | 7/2003 | Platz et al. |
| 6,595,205 B2 | 7/2003 | Andersson et al. |
| 6,595,208 B1 | 7/2003 | Coffee et al. |
| D478,983 S | 8/2003 | Whitehall et al. |
| 6,606,992 B1 | 8/2003 | Schuler et al. |
| D479,745 S | 9/2003 | Albulet et al. |
| 6,613,308 B2 | 9/2003 | Bartus et al. |
| 6,615,987 B1 | 9/2003 | Greenhill et al. |
| 6,620,910 B1 | 9/2003 | Calas et al. |
| 6,626,173 B2 | 9/2003 | Genova et al. |
| D480,806 S | 10/2003 | Engelbreth et al. |
| 6,630,169 B1 | 10/2003 | Bot et al. |
| 6,632,258 B1 | 10/2003 | Wheelock et al. |
| 6,632,456 B1 | 10/2003 | Backstrom et al. |
| 6,635,283 B2 | 10/2003 | Edwards et al. |
| 6,637,431 B2 | 10/2003 | Ekelius et al. |
| 6,640,050 B2 | 10/2003 | Nichols et al. |
| 6,644,309 B2 | 11/2003 | Casper et al. |
| 6,645,468 B2 | 11/2003 | Cutie et al. |
| 6,645,504 B1 | 11/2003 | Weiner et al. |
| 6,652,838 B2 | 11/2003 | Weinstein et al. |
| 6,652,885 B2 | 11/2003 | Steiner et al. |
| D483,860 S | 12/2003 | Knoch |
| 6,655,379 B2 | 12/2003 | Clark et al. |
| 6,655,380 B1 | 12/2003 | Andersson et al. |
| 6,655,381 B2 | 12/2003 | Keane et al. |
| 6,660,716 B1 | 12/2003 | Yakubu-Madus et al. |
| 6,663,898 B2 | 12/2003 | Milstein |
| 6,668,826 B1 | 12/2003 | Myrman et al. |
| 6,672,304 B1 | 1/2004 | Casper et al. |
| 6,676,931 B2 | 1/2004 | Dugger, III. |
| 6,679,255 B2 | 1/2004 | Pera |
| 6,681,767 B1 | 1/2004 | Patton et al. |
| 6,681,768 B2 | 1/2004 | Haaije de Boer et al. |
| 6,685,967 B1 | 2/2004 | Patton et al. |
| 6,698,421 B2 | 3/2004 | Attolini |
| 6,698,422 B2 | 3/2004 | Fugelsang et al. |
| 6,701,917 B2 | 3/2004 | O'Leary |
| 6,703,361 B2 | 3/2004 | Weiner et al. |
| 6,703,365 B2 | 3/2004 | Galloway et al. |
| 6,703,381 B1 | 3/2004 | Ekwuribe et al. |
| 6,705,313 B2 | 3/2004 | Niccolai |
| 6,715,486 B2 | 4/2004 | Gieschen et al. |
| 6,715,487 B2 | 4/2004 | Nichols et al. |
| 6,718,972 B2 | 4/2004 | O'Leary |
| 6,720,407 B1 | 4/2004 | Hughes et al. |
| 6,722,363 B1 | 4/2004 | von Schuckmann |
| D489,448 S | 5/2004 | Shayan |
| 6,729,324 B2 | 5/2004 | Casper et al. |
| 6,729,328 B2 | 5/2004 | Goldemann |
| 6,737,045 B2 | 5/2004 | Patton |
| 6,745,761 B2 | 6/2004 | Christrup et al. |
| 6,747,006 B2 | 6/2004 | Efendic |
| 6,748,946 B1 | 6/2004 | Rand et al. |
| 6,748,947 B2 | 6/2004 | Keane et al. |
| 6,752,145 B1 | 6/2004 | Bonney et al. |
| 6,755,190 B2 | 6/2004 | Rasmussen |
| D492,769 S | 7/2004 | Hatanaka |
| D493,220 S | 7/2004 | Burge et al. |
| D493,519 S | 7/2004 | Jonsson et al. |
| 6,774,112 B2 | 8/2004 | Gougoutas |
| 6,787,152 B2 | 9/2004 | Kirby et al. |
| 6,790,496 B1 | 9/2004 | Levander et al. |
| 6,792,945 B2 | 9/2004 | Davies et al. |
| 6,797,258 B2 | 9/2004 | Platz et al. |
| 6,799,572 B2 | 10/2004 | Nichols et al. |
| 6,800,643 B2 | 10/2004 | Cuenoud et al. |
| 6,803,044 B1 | 10/2004 | Catania et al. |
| 6,821,949 B2 | 11/2004 | Bridon et al. |
| 6,823,863 B2 | 11/2004 | Huxham et al. |
| D499,802 S | 12/2004 | Pinon et al. |
| 6,830,046 B2 | 12/2004 | Blakley et al. |
| 6,838,075 B2 | 1/2005 | Stevenson et al. |
| 6,838,076 B2 | 1/2005 | Patton et al. |
| 6,847,595 B2 | 1/2005 | Tanaka |
| 6,848,443 B2 | 2/2005 | Schmidt et al. |
| 6,849,708 B1 | 2/2005 | Habener |
| 6,852,690 B1 | 2/2005 | Nauck et al. |
| 6,858,199 B1 | 2/2005 | Edwards et al. |
| 6,860,262 B2 | 3/2005 | Christup et al. |
| 6,866,037 B1 | 3/2005 | Aslin et al. |
| 6,871,646 B2 | 3/2005 | Keane et al. |
| 6,871,647 B2 | 3/2005 | Allan et al. |
| 6,880,554 B1 | 4/2005 | Coffee |
| 6,881,423 B2 | 4/2005 | Dohi et al. |
| 6,884,435 B1 | 4/2005 | O'Hagan et al. |
| 6,887,459 B1 | 5/2005 | Haeberlin |
| 6,887,849 B2 | 5/2005 | Bridon et al. |
| 6,889,687 B1 | 5/2005 | Olsson |
| 6,892,728 B2 | 5/2005 | Helgesson et al. |
| 6,896,906 B2 | 5/2005 | Hastedt et al. |
| D506,680 S | 6/2005 | Saelzer |
| 6,904,907 B2 | 6/2005 | Speldrich et al. |
| 6,906,030 B2 | 6/2005 | Milstein |
| 6,916,354 B2 | 7/2005 | Elliott |
| 6,918,991 B2 | 7/2005 | Chickering, III et al. |
| 6,921,458 B2 | 7/2005 | Chickering, III et al. |
| 6,921,528 B2 | 7/2005 | Edwards et al. |

(56) References Cited

U.S. PATENT DOCUMENTS

| | | |
|---|---|---|
| 6,923,175 B2 | 8/2005 | Poole et al. |
| D509,296 S | 9/2005 | Minshull et al. |
| D509,898 S | 9/2005 | Bunce et al. |
| 6,948,496 B2 | 9/2005 | Eason et al. |
| 6,949,258 B2 | 9/2005 | Zhang |
| 6,951,215 B1 | 10/2005 | Hoffman |
| 6,953,812 B2 | 10/2005 | Jorgenson et al. |
| D511,208 S | 11/2005 | Pardonge et al. |
| D511,977 S | 11/2005 | Saelzer |
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Andersson et al. |
| 6,981,499 B2 | 1/2006 | Andersson et al. |
| 6,989,155 B1 | 1/2006 | Ganderton et al. |
| 6,991,779 B2 | 1/2006 | Steiner et al. |
| D515,696 S | 2/2006 | Lucking et al. |
| D515,924 S | 2/2006 | Grant |
| D516,211 S | 2/2006 | Minshull et al. |
| 6,998,387 B1 | 2/2006 | Goke et al. |
| D518,170 S | 3/2006 | Clarke et al. |
| D518,171 S | 3/2006 | Anderson et al. |
| 7,022,674 B2 | 4/2006 | DeFelippis et al. |
| 7,025,056 B2 | 4/2006 | Eason et al. |
| 7,028,686 B2 | 4/2006 | Gonda et al. |
| 7,030,084 B2 | 4/2006 | Ekwuribe et al. |
| 7,032,593 B2 | 4/2006 | Johnston et al. |
| 7,035,294 B2 | 4/2006 | Dove et al. |
| 7,047,967 B2 | 5/2006 | Knudsen |
| 7,048,908 B2 | 5/2006 | Basu et al. |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,084,243 B2 | 8/2006 | Glaesner et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,843 B2 | 9/2006 | Glaesner et al. |
| 7,101,866 B2 | 9/2006 | Biggadike et al. |
| 7,107,988 B2 | 9/2006 | Pinon et al. |
| D529,604 S | 10/2006 | Young et al. |
| 7,125,566 B2 | 10/2006 | Etter |
| 7,128,067 B2 | 10/2006 | Byron et al. |
| 7,131,441 B1 | 11/2006 | Keller et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,151,456 B2 | 12/2006 | Godfrey |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| 7,179,788 B2 | 2/2007 | DeFelippis et al. |
| D537,936 S | 3/2007 | Cox et al. |
| D538,423 S | 3/2007 | Berube et al. |
| 7,185,650 B2 | 3/2007 | Huber et al. |
| D540,671 S | 4/2007 | Born |
| D541,151 S | 4/2007 | Born |
| 7,198,806 B2 | 4/2007 | Berndt |
| 7,211,557 B2 | 5/2007 | DiMarchi et al. |
| 7,219,664 B2 | 5/2007 | Ruckdeschel et al. |
| 7,223,728 B2 | 5/2007 | Yakubu-Madus et al. |
| D544,093 S | 6/2007 | Eriksen |
| 7,231,919 B2 | 6/2007 | Giroux |
| 7,232,897 B2 | 6/2007 | Hotamisligil et al. |
| 7,234,459 B2 | 6/2007 | Del Bon |
| 7,234,460 B2 | 6/2007 | Greenleaf et al. |
| 7,234,464 B2 | 6/2007 | Goede et al. |
| 7,238,663 B2 | 7/2007 | DeFelippis et al. |
| 7,246,617 B1 | 7/2007 | Harmer et al. |
| D548,330 S | 8/2007 | Cox et al. |
| D548,618 S | 8/2007 | Ferguson et al. |
| D548,619 S | 8/2007 | Ferguson et al. |
| D548,833 S | 8/2007 | Young et al. |
| D549,111 S | 8/2007 | Ferguson et al. |
| 7,258,118 B2 | 8/2007 | Goede et al. |
| 7,259,233 B2 | 8/2007 | Dodd et al. |
| D550,835 S | 9/2007 | Tanaka et al. |
| 7,265,087 B1 | 9/2007 | Goke et al. |
| 7,270,124 B2 | 9/2007 | Rasmussen |
| D552,729 S | 10/2007 | Cox et al. |
| 7,276,534 B2 | 10/2007 | Milstein |
| 7,278,419 B2 | 10/2007 | Gonda |
| 7,278,426 B2 | 10/2007 | Myrman et al. |
| 7,278,843 B2 | 10/2007 | Feldstein et al. |
| 7,279,457 B2 | 10/2007 | Pohl et al. |
| 7,284,553 B2 | 10/2007 | Hochrainer |
| D557,799 S | 12/2007 | Greenhalgh et al. |
| 7,305,986 B1 | 12/2007 | Steiner |
| 7,306,787 B2 | 12/2007 | Tarara et al. |
| D560,793 S | 1/2008 | Pearl et al. |
| 7,314,859 B2 | 1/2008 | Green et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| D566,549 S | 4/2008 | Russell |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| 7,401,713 B2 | 7/2008 | Ede et al. |
| 7,402,564 B1 | 7/2008 | Schteingart et al. |
| 7,414,720 B2 | 8/2008 | Wachtel et al. |
| D577,815 S | 9/2008 | Gokhale et al. |
| 7,422,013 B2 | 9/2008 | Burr et al. |
| D579,549 S | 10/2008 | Birath et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| 7,453,556 B2 | 11/2008 | Hochrainer et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Yang et al. |
| 7,500,479 B2 | 3/2009 | Nichols et al. |
| 7,503,324 B2 | 3/2009 | Barney et al. |
| 7,504,538 B2 | 3/2009 | Chang et al. |
| 7,517,874 B2 | 4/2009 | Beckett et al. |
| 7,520,278 B2 | 4/2009 | Crowder et al. |
| 7,521,069 B2 | 4/2009 | Patton et al. |
| 7,533,668 B1 | 5/2009 | Widerstrom |
| D594,753 S | 6/2009 | Eadicicco et al. |
| 7,556,798 B2 | 7/2009 | Edwards et al. |
| 7,559,322 B2 | 7/2009 | Foley et al. |
| D597,418 S | 8/2009 | Stojek |
| D597,657 S | 8/2009 | Kinsey et al. |
| D598,785 S | 8/2009 | Stojek |
| 7,584,846 B2 | 9/2009 | Senter |
| 7,598,222 B2 | 10/2009 | Prouty, Jr. et al. |
| D604,832 S | 11/2009 | Smutney |
| D604,833 S | 11/2009 | Polidoro |
| D605,752 S | 12/2009 | Polidoro |
| D605,753 S | 12/2009 | Smutney |
| 7,625,865 B2 | 12/2009 | Colombo |
| 7,648,960 B2 | 1/2010 | Steiner et al. |
| D613,849 S | 4/2010 | Smutney |
| D614,045 S | 4/2010 | Gaudenzi et al. |
| D614,760 S | 4/2010 | Smutney et al. |
| 7,694,676 B2 | 4/2010 | Wachtel |
| 7,708,014 B2 | 5/2010 | Yamashita et al. |
| 7,709,639 B2 | 5/2010 | Stevenson |
| 7,713,937 B2 | 5/2010 | Schteingart et al. |
| 7,727,963 B2 | 6/2010 | Schteingart et al. |
| 7,735,485 B2 | 6/2010 | Yamashita et al. |
| D620,812 S | 8/2010 | Gaudenzi et al. |
| 7,794,754 B2 | 9/2010 | Feldstein et al. |

(56) References Cited

U.S. PATENT DOCUMENTS

| | | |
|---|---|---|
| 7,799,344 B2 | 9/2010 | Oberg |
| 7,803,404 B2 | 9/2010 | Hokenson |
| 7,820,676 B2 | 10/2010 | Leone-Bay et al. |
| D626,836 S | 11/2010 | Lien |
| D628,090 S | 11/2010 | Stuiber et al. |
| 7,833,549 B2 | 11/2010 | Steiner et al. |
| 7,833,550 B2 | 11/2010 | Steiner et al. |
| 7,842,662 B2 | 11/2010 | Schteingart et al. |
| D629,505 S | 12/2010 | Adamo |
| D629,506 S | 12/2010 | Adamo |
| D629,886 S | 12/2010 | Adamo |
| D629,887 S | 12/2010 | Adamo |
| D629,888 S | 12/2010 | Adamo |
| D635,241 S | 3/2011 | McLean |
| D635,242 S | 3/2011 | Adamo |
| D635,243 S | 3/2011 | Kinsey |
| 7,913,688 B2 | 3/2011 | Cross |
| D636,867 S | 4/2011 | Polidoro et al. |
| D636,868 S | 4/2011 | Kinsey et al. |
| D636,869 S | 4/2011 | Laurenzi et al. |
| 7,919,119 B2 | 4/2011 | Straub et al. |
| 7,943,178 B2 | 5/2011 | Steiner et al. |
| 7,943,572 B2 | 5/2011 | Cheatham et al. |
| 7,954,491 B2 | 6/2011 | Hrkach |
| 7,959,609 B2 | 6/2011 | Gaydos et al. |
| D641,076 S | 7/2011 | Grunstad et al. |
| D643,308 S | 8/2011 | Bergey |
| D645,954 S | 9/2011 | Hately |
| D647,195 S | 10/2011 | Clarke et al. |
| D647,196 S | 10/2011 | Clarke et al. |
| 8,037,880 B2 | 10/2011 | Zhu et al. |
| 8,037,881 B2 | 10/2011 | Pentafragas |
| 8,039,431 B2 | 10/2011 | Wilson et al. |
| 8,047,203 B2 | 11/2011 | Young et al. |
| D652,322 S | 1/2012 | Stuiber et al. |
| 8,109,267 B2 | 2/2012 | Villax et al. |
| 8,119,593 B2 | 2/2012 | Richardson |
| D655,622 S | 3/2012 | Sadler et al. |
| 8,133,514 B2 | 3/2012 | Milstein |
| 8,146,588 B2 | 4/2012 | Steiner et al. |
| 8,156,936 B2 | 4/2012 | Steiner et al. |
| D659,020 S | 5/2012 | Kemner |
| D659,022 S | 5/2012 | Kemner |
| D660,956 S | 5/2012 | Zuyderhoudt |
| 8,166,970 B2 | 5/2012 | Poole et al. |
| 8,172,817 B2 | 5/2012 | Michaels et al. |
| 8,196,576 B2 | 6/2012 | Kriksunov et al. |
| 8,201,555 B2 | 6/2012 | Chawla |
| 8,202,992 B2 | 6/2012 | Stevenson |
| D663,830 S | 7/2012 | Sears |
| D664,640 S | 7/2012 | Smutney et al. |
| 8,215,300 B2 | 7/2012 | Steiner et al. |
| 8,217,007 B1 | 7/2012 | Schteingart et al. |
| 8,227,409 B2 | 7/2012 | Kraft |
| 8,236,766 B2 | 8/2012 | Schteingart et al. |
| 8,252,916 B2 | 8/2012 | Simard et al. |
| 8,258,095 B2 | 9/2012 | Boss et al. |
| 8,278,308 B2 | 10/2012 | Leone-Bay et al. |
| 8,293,869 B2 | 10/2012 | Bossard |
| 8,314,106 B2 | 11/2012 | Kraft |
| D671,842 S | 12/2012 | Bergey |
| D674,893 S | 1/2013 | Kinsey et al. |
| 8,372,804 B2 | 2/2013 | Richardson |
| 8,377,869 B2 | 2/2013 | Richardson |
| 8,389,470 B2 | 3/2013 | Steiner |
| 8,394,414 B2 | 3/2013 | Steiner et al. |
| 8,408,200 B2 | 4/2013 | Clark et al. |
| 8,420,604 B2 | 4/2013 | Hokenson |
| 8,424,518 B2 | 4/2013 | Smutney |
| 8,485,180 B2 | 7/2013 | Smutney et al. |
| 8,486,894 B2 | 7/2013 | Schteingart et al. |
| 8,499,757 B2 | 8/2013 | Smutney |
| 8,512,932 B2 | 8/2013 | Wilson et al. |
| 8,522,775 B2 | 9/2013 | Malhotra et al. |
| 8,536,131 B2 | 9/2013 | Schteingart et al. |
| 8,538,707 B2 | 9/2013 | Adamo et al. |
| 8,539,946 B2 | 9/2013 | Esteve et al. |
| 8,551,528 B2 | 10/2013 | Grant et al. |
| 8,563,101 B2 | 10/2013 | Spallek |
| 8,636,001 B2 | 1/2014 | Smutney |
| 8,642,548 B2 | 2/2014 | Richardson et al. |
| 8,671,937 B2 | 3/2014 | Steiner et al. |
| 8,677,992 B2 | 3/2014 | Villax |
| 8,763,606 B2 | 7/2014 | Mosier et al. |
| 8,778,403 B2 | 7/2014 | Grant et al. |
| 8,783,249 B2 | 7/2014 | Trent et al. |
| D711,740 S | 8/2014 | Lien |
| 8,808,786 B2 | 8/2014 | Jinks et al. |
| 8,820,324 B2 | 9/2014 | Smith et al. |
| 8,909,487 B2 | 12/2014 | Adamo et al. |
| 8,925,726 B2 | 1/2015 | Bergey |
| 9,041,925 B2 | 5/2015 | Adamo et al. |
| 9,138,407 B2 | 9/2015 | Caponetti et al. |
| 2001/0020147 A1 | 9/2001 | Staniforth et al. |
| 2001/0039442 A1 | 11/2001 | Gorge et al. |
| 2002/0000225 A1 | 1/2002 | Schuler et al. |
| 2002/0033177 A1 | 3/2002 | Ohki et al. |
| 2002/0052381 A1 | 5/2002 | Bar-Or et al. |
| 2002/0053344 A1 | 5/2002 | Davies et al. |
| 2002/0053347 A1 | 5/2002 | Ziaee |
| 2002/0065239 A1 | 5/2002 | Caplan et al. |
| 2002/0088462 A1 | 7/2002 | Genova et al. |
| 2002/0101590 A1 | 8/2002 | Shimaoka |
| 2002/0144680 A1 | 10/2002 | Nilsson et al. |
| 2002/0161001 A1 | 10/2002 | Kanstrup et al. |
| 2003/0000524 A1 | 1/2003 | Andersson et al. |
| 2003/0010794 A1 | 1/2003 | Herdtle et al. |
| 2003/0013641 A1 | 1/2003 | Steiner et al. |
| 2003/0017211 A1 | 1/2003 | Steiner |
| 2003/0053960 A1 | 3/2003 | Heijerman et al. |
| 2003/0064097 A1 | 4/2003 | Patel et al. |
| 2003/0068378 A1 | 4/2003 | Chen et al. |
| 2003/0099636 A1 | 5/2003 | Epshtein et al. |
| 2003/0136405 A1 | 7/2003 | Goede et al. |
| 2003/0194420 A1 | 10/2003 | Holl et al. |
| 2003/0235538 A1 | 12/2003 | Zierenberg |
| 2004/0024180 A1 | 2/2004 | Drauz |
| 2004/0025875 A1 | 2/2004 | Reber et al. |
| 2004/0034014 A1 | 2/2004 | Kanstrup et al. |
| 2004/0038865 A1 | 2/2004 | Gelber et al. |
| 2004/0053819 A1 | 3/2004 | Dodd et al. |
| 2004/0062722 A1 | 4/2004 | Gonda et al. |
| 2004/0076588 A1 | 4/2004 | Batycky et al. |
| 2004/0077528 A1 | 4/2004 | Steiner et al. |
| 2004/0096403 A1 | 5/2004 | Steiner |
| 2004/0107963 A1 | 6/2004 | Finlay et al. |
| 2004/0121964 A1 | 6/2004 | Madar et al. |
| 2004/0138099 A1 | 7/2004 | Draeger |
| 2004/0151059 A1 | 8/2004 | Robert, II et al. |
| 2004/0151774 A1 | 8/2004 | Pauletti et al. |
| 2004/0157928 A1 | 8/2004 | Kim et al. |
| 2004/0163648 A1 | 8/2004 | Burton |
| 2004/0182387 A1 | 9/2004 | Steiner et al. |
| 2004/0187869 A1 | 9/2004 | Bjorndal et al. |
| 2004/0204439 A1 | 10/2004 | Staniforth et al. |
| 2004/0204440 A1 | 10/2004 | Staniforth et al. |
| 2004/0211419 A1 | 10/2004 | Eason et al. |
| 2004/0211420 A1 | 10/2004 | Minshull |
| 2004/0234615 A1 | 11/2004 | Sabetsky |
| 2004/0234616 A1 | 11/2004 | Sabetsky |
| 2004/0241232 A1 | 12/2004 | Brown et al. |
| 2004/0247628 A1 | 12/2004 | Lintz et al. |
| 2004/0250812 A1 | 12/2004 | Davies et al. |
| 2005/0000518 A1 | 1/2005 | Dunkley et al. |
| 2005/0039743 A1 | 2/2005 | Taylor |
| 2005/0043228 A1 | 2/2005 | DeFelippis et al. |
| 2005/0043247 A1 | 2/2005 | Trunk et al. |
| 2005/0056281 A1 | 3/2005 | Snow |
| 2005/0070469 A1 | 3/2005 | Bloom |
| 2005/0080000 A1 | 4/2005 | Thurow et al. |
| 2005/0119604 A1 | 6/2005 | Bonney et al. |
| 2005/0124644 A1 | 6/2005 | Nilsson et al. |
| 2005/0147581 A1 | 7/2005 | Zamiri et al. |
| 2005/0153874 A1 | 7/2005 | Cheatham et al. |

(56) References Cited

U.S. PATENT DOCUMENTS

| | | |
|---|---|---|
| 2005/0155601 A1 | 7/2005 | Steiner et al. |
| 2005/0183723 A1 | 8/2005 | Pinon et al. |
| 2005/0187749 A1 | 8/2005 | Singley |
| 2005/0214251 A1 | 9/2005 | Pohl et al. |
| 2005/0252508 A1 | 11/2005 | Koerner |
| 2005/0265927 A1 | 12/2005 | Lee |
| 2005/0274378 A1 | 12/2005 | Bonney et al. |
| 2006/0000469 A1 | 1/2006 | Tseng |
| 2006/0003316 A1 | 1/2006 | Simard et al. |
| 2006/0040953 A1 | 2/2006 | Leone-Bay et al. |
| 2006/0041133 A1 | 2/2006 | Stevenson et al. |
| 2006/0062740 A1 | 3/2006 | Rand |
| 2006/0099269 A1 | 5/2006 | Cheatham et al. |
| 2006/0120969 A1 | 6/2006 | Nilsson et al. |
| 2006/0153778 A1 | 7/2006 | Gelber et al. |
| 2006/0160722 A1 | 7/2006 | Green et al. |
| 2006/0165756 A1 | 7/2006 | Catani et al. |
| 2006/0239933 A1 | 10/2006 | Nilsson et al. |
| 2006/0239934 A1 | 10/2006 | Cheatham et al. |
| 2006/0243275 A1 | 11/2006 | Ruckdeschel et al. |
| 2006/0249419 A1 | 11/2006 | Taylor et al. |
| 2006/0260777 A1 | 11/2006 | Rashba-Step et al. |
| 2006/0283758 A1 | 12/2006 | Pasbrig |
| 2007/0006876 A1 | 1/2007 | Finlay et al. |
| 2007/0017506 A1 | 1/2007 | Bell et al. |
| 2007/0020191 A1 | 1/2007 | Boss et al. |
| 2007/0027063 A1 | 2/2007 | Boss et al. |
| 2007/0044793 A1 | 3/2007 | Kleinstreuer et al. |
| 2007/0049576 A1 | 3/2007 | Barlow et al. |
| 2007/0059373 A1 | 3/2007 | Oberg |
| 2007/0059374 A1 | 3/2007 | Hokenson et al. |
| 2007/0074989 A1 | 4/2007 | Merboth et al. |
| 2007/0077219 A1 | 4/2007 | Fahl et al. |
| 2007/0086952 A1 | 4/2007 | Steiner |
| 2007/0099454 A1 | 5/2007 | Gordon |
| 2007/0125375 A1 | 6/2007 | Finlay et al. |
| 2007/0128193 A1 | 6/2007 | O'Neil et al. |
| 2007/0151562 A1 | 7/2007 | Jones |
| 2007/0175314 A1 | 8/2007 | Wanne |
| 2007/0191462 A1 | 8/2007 | Hettiarachchi |
| 2007/0196503 A1 | 8/2007 | Wilson et al. |
| 2007/0207958 A1 | 9/2007 | Bridon et al. |
| 2007/0225587 A1 | 9/2007 | Burnell et al. |
| 2007/0235029 A1 | 10/2007 | Zhu et al. |
| 2007/0240708 A1 | 10/2007 | Schuckmann |
| 2007/0272763 A1 | 11/2007 | Dunne et al. |
| 2007/0277820 A1 | 12/2007 | Crowder et al. |
| 2007/0277821 A1 | 12/2007 | Oliva et al. |
| 2007/0295332 A1 | 12/2007 | Ziegler |
| 2007/0299074 A1 | 12/2007 | Netz et al. |
| 2008/0008764 A1 | 1/2008 | Milstein |
| 2008/0015457 A1 | 1/2008 | Silva |
| 2008/0047550 A2 | 2/2008 | Steiner et al. |
| 2008/0066739 A1 | 3/2008 | LeMahieu et al. |
| 2008/0108554 A1 | 5/2008 | Jackson et al. |
| 2008/0108574 A1 | 5/2008 | Barlow et al. |
| 2008/0115785 A1 | 5/2008 | Eason et al. |
| 2008/0127970 A1 | 6/2008 | Steiner et al. |
| 2008/0127971 A1 | 6/2008 | King et al. |
| 2008/0127974 A1 | 6/2008 | Lastow |
| 2008/0168987 A1 | 7/2008 | Denny et al. |
| 2008/0190424 A1 | 8/2008 | Lucking et al. |
| 2008/0197044 A1 | 8/2008 | Hickey et al. |
| 2008/0216824 A1 | 9/2008 | Ooida |
| 2008/0217199 A1 | 9/2008 | Burress et al. |
| 2008/0255468 A1 | 10/2008 | Derchak et al. |
| 2008/0260838 A1 | 10/2008 | Hokenson et al. |
| 2008/0260840 A1 | 10/2008 | Alessi |
| 2008/0295833 A1 | 12/2008 | Rohrschneider et al. |
| 2008/0314384 A1 | 12/2008 | Harris et al. |
| 2008/0319333 A1 | 12/2008 | Gavish et al. |
| 2009/0025720 A1 | 1/2009 | Chen |
| 2009/0068274 A1 | 3/2009 | Edwards et al. |
| 2009/0084379 A1 | 4/2009 | Goeckner et al. |
| 2009/0084380 A1 | 4/2009 | Gieschen et al. |
| 2009/0134051 A1 | 5/2009 | Rapp et al. |
| 2009/0149727 A1 | 6/2009 | Truitt et al. |
| 2009/0151720 A1 | 6/2009 | Inoue et al. |
| 2009/0178676 A1 | 7/2009 | Villax et al. |
| 2009/0205657 A1 | 8/2009 | Barney et al. |
| 2009/0209502 A1 | 8/2009 | Haeberlin et al. |
| 2009/0232891 A1 | 9/2009 | Gelber et al. |
| 2009/0241949 A1 | 10/2009 | Smutney |
| 2009/0250058 A1 | 10/2009 | Lastow |
| 2009/0258818 A1 | 10/2009 | Surolia et al. |
| 2009/0314292 A1 | 12/2009 | Overfield |
| 2009/0320837 A1 | 12/2009 | Smith et al. |
| 2010/0012120 A1 | 1/2010 | Herder |
| 2010/0086609 A1 | 4/2010 | Steiner et al. |
| 2010/0113363 A1 | 5/2010 | Holst et al. |
| 2010/0163042 A1 | 7/2010 | Bhowmick et al. |
| 2010/0180894 A1 | 7/2010 | Jones et al. |
| 2010/0181225 A1 | 7/2010 | Spallek et al. |
| 2010/0190701 A1 | 7/2010 | Day et al. |
| 2010/0193380 A1 | 8/2010 | Sullivan et al. |
| 2010/0197565 A1 | 8/2010 | Smutney et al. |
| 2010/0212667 A1 | 8/2010 | Smith et al. |
| 2010/0235116 A1 | 9/2010 | Adamo et al. |
| 2010/0238457 A1 | 9/2010 | Adamo et al. |
| 2010/0278924 A1 | 11/2010 | Oberg |
| 2010/0288276 A1 | 11/2010 | Ganderton et al. |
| 2010/0326438 A1 | 12/2010 | Dunne |
| 2011/0000482 A1 | 1/2011 | Gumaste et al. |
| 2011/0003004 A1 | 1/2011 | Hokenson |
| 2011/0011394 A1 | 1/2011 | Edwards et al. |
| 2011/0083667 A1 | 4/2011 | Briant |
| 2011/0158935 A1 | 6/2011 | Kraft |
| 2011/0183901 A1 | 7/2011 | Cheatham |
| 2012/0014999 A1 | 1/2012 | Grant et al. |
| 2012/0040899 A1 | 2/2012 | Costello |
| 2012/0071510 A1 | 3/2012 | Leone-Bay et al. |
| 2012/0094905 A1 | 4/2012 | Costello |
| 2012/0115777 A1 | 5/2012 | Richardson |
| 2012/0122775 A1 | 5/2012 | Boss et al. |
| 2012/0160241 A1 | 6/2012 | Oliva |
| 2012/0164186 A1 | 6/2012 | Grant et al. |
| 2012/0178935 A1 | 7/2012 | Stevenson |
| 2012/0192865 A1 | 8/2012 | Steiner et al. |
| 2012/0207913 A1 | 8/2012 | Smyth |
| 2012/0240929 A1 | 9/2012 | Steiner et al. |
| 2012/0247235 A1 | 10/2012 | Adamo et al. |
| 2012/0247465 A1 | 10/2012 | Wachtel |
| 2012/0328676 A1 | 12/2012 | Leone-Bay et al. |
| 2013/0012710 A1 | 1/2013 | Freeman et al. |
| 2013/0053309 A1 | 2/2013 | Kraft |
| 2013/0104887 A1 | 5/2013 | Smutney et al. |
| 2013/0118491 A1 | 5/2013 | Richardson et al. |
| 2013/0125886 A1 | 5/2013 | Richardson et al. |
| 2013/0143801 A1 | 6/2013 | Steiner et al. |
| 2013/0189365 A1 | 7/2013 | Hokenson |
| 2013/0199527 A1 | 8/2013 | Smutney et al. |
| 2013/0289278 A1 | 10/2013 | Kraft |
| 2013/0291866 A1 | 11/2013 | Smutney |
| 2013/0291867 A1 | 11/2013 | Smutney |
| 2013/0303445 A1 | 11/2013 | Wilson et al. |
| 2013/0338065 A1 | 12/2013 | Smutney |
| 2014/0007873 A1 | 1/2014 | Smutney |
| 2014/0014106 A1 | 1/2014 | Smutney |
| 2014/0083421 A1 | 3/2014 | Smutney |
| 2014/0096771 A1 | 4/2014 | Remmelgas et al. |
| 2014/0100158 A1 | 4/2014 | Richardson et al. |
| 2014/0187490 A1 | 7/2014 | Richardson et al. |
| 2014/0199398 A1 | 7/2014 | Grant et al. |
| 2014/0227359 A1 | 8/2014 | Leone-Bay et al. |
| 2014/0243530 A1 | 8/2014 | Stevenson et al. |
| 2014/0271888 A1 | 9/2014 | Grant et al. |
| 2014/0290654 A1 | 10/2014 | Poole et al. |
| 2014/0302151 A1 | 10/2014 | Leone-Bay et al. |
| 2014/0308358 A1 | 10/2014 | Oberg et al. |
| 2014/0315953 A1 | 10/2014 | Leone-Bay et al. |
| 2015/0031609 A1 | 1/2015 | Steiner et al. |
| 2015/0045295 A1 | 2/2015 | Smutney et al. |
| 2015/0052977 A1 | 2/2015 | Adamo et al. |
| 2015/0065422 A1 | 3/2015 | Kraft |

(56) References Cited

U.S. PATENT DOCUMENTS

| | | |
|---|---|---|
| 2015/0080298 A1 | 3/2015 | Costello et al. |
| 2015/0108023 A1 | 4/2015 | Bergey |
| 2015/0122258 A1 | 5/2015 | Steiner et al. |
| 2015/0150980 A1 | 6/2015 | Leone-Bay et al. |
| 2015/0174210 A1 | 6/2015 | Boss et al. |
| 2015/0196724 A1 | 7/2015 | Adamo et al. |
| 2015/0226656 A1 | 8/2015 | Adamo et al. |
| 2015/0231067 A1 | 8/2015 | Mann |
| 2015/0246188 A1 | 9/2015 | Steiner et al. |
| 2015/0283069 A1 | 10/2015 | Smutney et al. |
| 2015/0283213 A1 | 10/2015 | Costello et al. |
| 2015/0290132 A1 | 10/2015 | Gelber et al. |
| 2015/0359744 A1 | 12/2015 | Hokenson et al. |

FOREIGN PATENT DOCUMENTS

| | | |
|---|---|---|
| CN | 101851213 | 10/2010 |
| DE | 2840442 C2 | 2/1982 |
| DE | 3639836 A1 | 6/1988 |
| DE | 19519840 A1 | 12/1996 |
| EP | 69715 | 1/1983 |
| EP | 122036 | 10/1984 |
| EP | 143524 | 6/1985 |
| EP | 180543 | 5/1986 |
| EP | 220958 | 5/1987 |
| EP | 237507 | 8/1987 |
| EP | 257915 | 2/1988 |
| EP | 308637 A1 | 3/1989 |
| EP | 360340 | 3/1990 |
| EP | 364235 | 4/1990 |
| EP | 387222 A | 9/1990 |
| EP | 388621 A | 9/1990 |
| EP | 606486 | 12/1993 |
| EP | 581473 A1 | 2/1994 |
| EP | 655237 | 5/1995 |
| EP | 666085 A1 | 8/1995 |
| EP | 748213 | 12/1996 |
| EP | 558879 B1 | 5/1997 |
| EP | 844007 | 12/1998 |
| EP | 1060741 A1 | 12/2000 |
| EP | 1114644 | 7/2001 |
| EP | 640354 B1 | 12/2001 |
| EP | 1364967 | 11/2003 |
| EP | 825885 B1 | 3/2004 |
| EP | 96911738 | 6/2004 |
| EP | 1598066 | 11/2005 |
| EP | 833652 B1 | 2/2008 |
| EP | 1923087 A2 | 5/2008 |
| EP | 2060268 A1 | 5/2009 |
| EP | 2314298 A1 | 4/2011 |
| GB | 475440 A | 11/1937 |
| GB | 716815 | 10/1954 |
| GB | 2072536 A | 10/1981 |
| GB | 2148841 A | 6/1985 |
| GB | 2240337 | 7/1991 |
| GB | 2253200 A | 9/1992 |
| GB | 2262452 | 6/1993 |
| GB | 2398065 A | 8/2004 |
| JP | 63-020301 | 1/1988 |
| JP | 2115154 A | 4/1990 |
| JP | 2-149545 | 2/1992 |
| JP | H07-041428 | 2/1995 |
| JP | 09-208485 | 8/1997 |
| JP | 10234827 A | 9/1998 |
| JP | 2002322294 | 11/2002 |
| JP | 2003-503420 | 1/2003 |
| JP | 2004-121061 | 4/2004 |
| JP | 2006-280620 A | 10/2006 |
| JP | 2007-061281 | 3/2007 |
| TW | 200505517 A | 2/2005 |
| WO | 90/13285 | 11/1990 |
| WO | 91/04011 | 4/1991 |
| WO | 91/06287 | 5/1991 |
| WO | 91/16038 | 10/1991 |
| WO | 91/16882 | 11/1991 |
| WO | 91/19524 | 12/1991 |
| WO | 92/04069 | 3/1992 |
| WO | 92/08509 | 5/1992 |
| WO | 93/02712 | 2/1993 |
| WO | 93/14110 | 7/1993 |
| WO | 93/17728 | 9/1993 |
| WO | 93/18754 A1 | 9/1993 |
| WO | 94/00291 | 1/1994 |
| WO | 94/08552 | 4/1994 |
| WO | 94/08599 | 4/1994 |
| WO | 94/19041 | 9/1994 |
| WO | 94/23702 | 10/1994 |
| WO | 94/25005 A1 | 11/1994 |
| WO | 95/00127 A1 | 1/1995 |
| WO | 95/05208 | 2/1995 |
| WO | 95/11666 | 5/1995 |
| WO | 95/24183 A1 | 9/1995 |
| WO | 95/31979 | 11/1995 |
| WO | 95/34294 | 12/1995 |
| WO | 96/01105 | 1/1996 |
| WO | 96/05810 | 2/1996 |
| WO | 96/13250 | 5/1996 |
| WO | 96/22802 A | 8/1996 |
| WO | 96/27386 A1 | 9/1996 |
| WO | 96/32149 | 10/1996 |
| WO | 96/36314 | 11/1996 |
| WO | 96/36317 A1 | 11/1996 |
| WO | 96/40206 A1 | 12/1996 |
| WO | 97/01365 | 1/1997 |
| WO | 97/04747 | 2/1997 |
| WO | 97/25086 A2 | 7/1997 |
| WO | 97/30743 | 8/1997 |
| WO | 97/35562 A1 | 10/1997 |
| WO | 97/46206 | 12/1997 |
| WO | 97/49386 | 12/1997 |
| WO | 98/26827 A1 | 6/1998 |
| WO | 98/39043 | 9/1998 |
| WO | 98/41255 A2 | 9/1998 |
| WO | 98/43615 | 10/1998 |
| WO | 99/14239 A1 | 3/1999 |
| WO | 99/18939 A1 | 4/1999 |
| WO | 99/32510 A1 | 7/1999 |
| WO | 99/33862 | 7/1999 |
| WO | 99/52506 | 10/1999 |
| WO | 00/12116 | 3/2000 |
| WO | 00/33811 A2 | 6/2000 |
| WO | 00/59476 A1 | 10/2000 |
| WO | 00/71154 A2 | 11/2000 |
| WO | 01/00654 | 1/2001 |
| WO | 01/81321 A | 1/2001 |
| WO | 01/07107 | 2/2001 |
| WO | 01/49274 A2 | 7/2001 |
| WO | 01/51071 | 7/2001 |
| WO | 01/52813 A1 | 7/2001 |
| WO | 01/66064 | 9/2001 |
| WO | 01/68169 | 9/2001 |
| WO | 01/97886 A1 | 12/2001 |
| WO | 02/11676 | 2/2002 |
| WO | 02/12201 A1 | 2/2002 |
| WO | 02/47659 A2 | 6/2002 |
| WO | 02/058735 | 8/2002 |
| WO | 02/059574 A1 | 8/2002 |
| WO | 02/067995 A1 | 9/2002 |
| WO | 02/085281 | 10/2002 |
| WO | 02/098348 | 12/2002 |
| WO | 02/102444 | 12/2002 |
| WO | 03/000202 | 1/2003 |
| WO | 03/022304 A1 | 3/2003 |
| WO | 03/055547 A1 | 7/2003 |
| WO | 03/057170 | 7/2003 |
| WO | 03/061578 A2 | 7/2003 |
| WO | 03/072195 A2 | 9/2003 |
| WO | 03/080149 A2 | 10/2003 |
| WO | 03/086345 | 10/2003 |
| WO | 03/094951 | 11/2003 |
| WO | 2004/012672 | 2/2004 |
| WO | 2004/012720 | 2/2004 |
| WO | 2004/033010 | 4/2004 |
| WO | 2004/035121 | 4/2004 |

(56) References Cited

FOREIGN PATENT DOCUMENTS

| | | |
|---|---|---|
| WO | 2004/041338 | 5/2004 |
| WO | 2004/050152 | 6/2004 |
| WO | 2004/054647 A1 | 7/2004 |
| WO | 2004/056314 | 7/2004 |
| WO | 2004/060458 | 7/2004 |
| WO | 2004/064862 | 8/2004 |
| WO | 2004/075919 | 9/2004 |
| WO | 2004/080401 | 9/2004 |
| WO | 2004/080482 | 9/2004 |
| WO | 2004/103304 A2 | 12/2004 |
| WO | 2005/020964 | 3/2005 |
| WO | 2005/023348 A | 3/2005 |
| WO | 2005/028699 A1 | 3/2005 |
| WO | 2005/067964 | 7/2005 |
| WO | 2005/081977 A2 | 9/2005 |
| WO | 2005/089722 | 9/2005 |
| WO | 2005/089843 | 9/2005 |
| WO | 2005/102428 A1 | 11/2005 |
| WO | 2005/102429 | 11/2005 |
| WO | 2005/113042 A1 | 12/2005 |
| WO | 2005/113043 | 12/2005 |
| WO | 2005/120616 | 12/2005 |
| WO | 2006/010248 | 2/2006 |
| WO | 2006/017688 A2 | 2/2006 |
| WO | 2006/023849 | 3/2006 |
| WO | 2006/023943 | 3/2006 |
| WO | 2006/023944 | 3/2006 |
| WO | 2006/037636 | 4/2006 |
| WO | 2006/059939 | 6/2006 |
| WO | 2006/061637 A2 | 6/2006 |
| WO | 2006/086107 A2 | 8/2006 |
| WO | 2006/090149 | 8/2006 |
| WO | 2006/105501 | 10/2006 |
| WO | 2007/007110 A1 | 1/2007 |
| WO | 2007/016600 A2 | 2/2007 |
| WO | 2007/019229 | 2/2007 |
| WO | 2007/024953 A1 | 3/2007 |
| WO | 2007/030706 | 3/2007 |
| WO | 2007/033316 | 3/2007 |
| WO | 2007/033372 A2 | 3/2007 |
| WO | 2007/042822 | 4/2007 |
| WO | 2007/068896 | 6/2007 |
| WO | 2007/075534 A2 | 7/2007 |
| WO | 2007/093310 | 8/2007 |
| WO | 2007/098500 | 8/2007 |
| WO | 2007/100535 | 9/2007 |
| WO | 2007/118342 | 10/2007 |
| WO | 2007/118343 A1 | 10/2007 |
| WO | 2007/121411 | 10/2007 |
| WO | 2007/132217 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/014613 A1 | 2/2008 |
| WO | 2008/020217 | 2/2008 |
| WO | 2008/060484 A2 | 5/2008 |
| WO | 2008/092864 | 8/2008 |
| WO | 2008/110809 | 9/2008 |
| WO | 2009/005546 A1 | 1/2009 |
| WO | 2009/008001 A2 | 1/2009 |
| WO | 2009/009013 A2 | 1/2009 |
| WO | 2009/047281 A1 | 4/2009 |
| WO | 2009/055030 | 4/2009 |
| WO | 2009/055740 | 4/2009 |
| WO | 2009/055742 | 4/2009 |
| WO | 2009/095684 A1 | 8/2009 |
| WO | 2009/121020 A1 | 10/2009 |
| WO | 2009/140587 A1 | 11/2009 |
| WO | 2009/152477 A2 | 12/2009 |
| WO | 2009/155581 A1 | 12/2009 |
| WO | 2010/021879 A2 | 2/2010 |
| WO | 2010/078373 A1 | 7/2010 |
| WO | 2010/080964 | 7/2010 |
| WO | 2010/102148 | 9/2010 |
| WO | 2010/105094 A1 | 9/2010 |
| WO | 2010/108046 A1 | 9/2010 |
| WO | 2010/125103 A1 | 11/2010 |
| WO | 2010/144785 A2 | 12/2010 |
| WO | 2010/144789 | 12/2010 |
| WO | 2011/017554 A2 | 2/2011 |
| WO | 2011/056889 A1 | 5/2011 |
| WO | 2011/163272 | 12/2011 |
| WO | 2012/064892 A1 | 5/2012 |
| WO | 2012/135765 | 10/2012 |
| WO | 2012/174472 A1 | 12/2012 |
| WO | 2012/174556 A1 | 12/2012 |
| WO | 2013/063160 A1 | 5/2013 |
| WO | 2014/012069 A2 | 1/2014 |
| WO | 2014/036323 A1 | 3/2014 |
| WO | 2014/066856 A1 | 5/2014 |
| WO | 2014/144895 A1 | 9/2014 |
| WO | 2015/010092 A1 | 1/2015 |
| WO | 2015/021064 A1 | 2/2015 |
| WO | 2015/148905 A1 | 10/2015 |

OTHER PUBLICATIONS

"An inhaled insulin formulation (Technosphere Insulin) effectively improves glycaemic control in patients with type 2 diabetes mellitus." Inpharma Weekly, vol. 1522, Jan. 28, 2006, p. 8.
ACTOS Product Insert. Aug. 2008.
"Adjusting Mealtime Insulin Doses." BD Diabetes. http://www.bd.com/diabetes/page.aspx?cat=7001&id=7280 (2014).
Ahren "GLP-1 and extra-islet effects." Horm. Med Res 36:842, 2004.
Ahren B et al. "Characterization of GLP-1 effects on b-cell function after meal ingestion in humans." Diabetes Care 26:2860, 2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.
Alabraba et al. Diabetes Technology & Therapeutics. Jul. 2009, 11(7): 427-430.
Alcohols limited. Alcohol speciality solvents—Go green! Jul. 24, 2010. Available from: <http://webarchive.org/web/20100724193725/http://www.alcohols.co.uk/speciality_solvents.php>.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
Al-Showair et al., Can all patients with COPD use the correct inhalation flow with all inhalers and does training help? Respiratory Medicine, vol. 101, No. 11, p. 2395-2401 (2007).
American Diabetes Association, "Standards of medical care in diabetes—2009", Diabetes Care, Jan. 2009, 32 Suppl 1: S13-61.
Amin N, Boss AH, Petrucci R, et al. Pulmonary functions (over 2 years) in diabetic subjects treated with AFRESA® or usual antidiabetic treatment ADA 2009; Poster 570.
Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.
Amin N, Marino MT, Cassidy JP, et al. Acute pulmonary effects of Technosphere® insulin inhalation powder administered using a Gen2B inhaler compared to MedTone® C inhaler. Diabetes Technology Meeting 2010; poster.
Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.

(56) References Cited

OTHER PUBLICATIONS

Angelo et al., Technosphere Insulin: Defining the Role of Technosphere Particles at the Celluar Level. J. Diabetes Sci. Technol., vol. 3, Issue 3, pp. 545-554 (2009).
Angelo et al. Technosphere® insulin inhalation powder: Defining the mechanism of action. ADA 2008; 57: Poster 428-P.
Antosiewiez et al., Prediction of pH-dependent properties of proteins. J Mol. Biol., 238:415-436 (1994).
Arakawa et al., Preferential interactions determine protein solubility in three-component solutions: the MgCl2 system. Biochemistry, 29:1914-1923 (1990).
Ashwell et al. "Twice-daily compared with once-daily insulin glargine in people with Type 1 diabetes using meal-time insulin aspart." 2006 Diabetes UK, Diabetic Medicine, 23, 879-886.
Ashwell et al., "Optimal timing of injection of once-daily insulin gargine in people with Type 1 diabetes using insulin lispro at meal-times" 2005 Diabetes UK, Diabetic Medicine, 23, 46-52.
Atherton, F. et al. "Synthesis of 2(R)-A3(S)-Acylamino-2-OXO-1-Azetidinyloxy U-Acetic Acids." Tetrahedron, vol. 40, No. 6, Jan. 1, 1984, pp. 1039-1046.
Avandia Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Drucker et al., Minireview: The glucagon-like peptides. Endocrinology, vol. 142, No. 2, pp. 521-527 (2001).
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled human insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al., "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder: results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.
Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73: 1721-1724 (1984).
Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Berge et al., "Pharmaceutical Salts", J. Pharmaceutical Sciences, Review Article, 66(1):1-19 (1977).
Bergenstal R, Kapsner P, Rendell M, et al., Comparative efficacy and safety of AFRESA® and a rapid-acting analog both given with glargine in subjects with T1 DM in a 52-week study ADA 2009; Poster 479.
Bergeron et al. "Macromolecular Self-Assembly of Diketopiperazine Tetrapeptides." J. Am. Chem. Soc. 116, 8479-8484, 1994.
Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Boer et al., Design and application of a new modular adapter for laser diffraction characterization of inhalation aerosols. International Jornal of Pharmaceutics 249, pp. 233-245 (2002).
Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere®/Insulin inhalation to mimic first

(56) References Cited

OTHER PUBLICATIONS phase insulin release." Presented at the 5th Annual Meeting of the Diabetes Technology Society, Nov. 2005, abstract A14.

Boss AH et al. "Markedly reduced post prandial glucose excursions through inhaled Technosphere®/Insulin in comparison to SC injected regular insulin in subjects with type 2 diabetes." 1st Annual Meeting of the European Association for the Study of Diabetes, Sep. 2005, abstract 816.

Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.

Boss et al. "Prandial Insulin: Is Inhaled Enough?" Drug Development Research 69(3):138-142 (2008).

Boss A H, Petrucci R, Lorber D. Coverage of prandial insulin requirements by means of an ultra-rapid-acting inhaled insulin. Journal of diabetes science and technology 2012;6:773-779.

Boss AH, Baughman RA, Evans SH, et al. A 3 month comparison in type 1 diabetes of inhaled Technosphere®/Insulin (TI) to Sc administered rapid-acting insulin analogue (RAA) as prandial insulin in a basal/prandial regimen. Diabetes 2006; 55:A97.

Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.

Boss AH, Evans, SH, Ren, H, et al. Superior post prandial glucose control in patients with type 1 diabetes when using prandial technosphere insulin compared to NovoLog. Diabetologia 2006; Abstract 181.

Boss AH, Marino MT, Cassidy JP, et al. C-peptide correction method to determine exogenous insulin levels in pharmacokinetic studies using Technosphere® insulin. Diabetologia 2009; 52 (suppl 1).

Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).

Brandt D, Boss AH. The next generation insulin therapy. OndrugDelivery 2006 (published online).

Brange et al., "Insulin Structure and Stability", Pharm Biotechnol, 5:315-50 (1993).

Bray "Exanatide" Am J Health-Sys Pharm 63:411, 2006.

Brownlee et al. "Glycemic variability: a hemoglobin A1c-independent risk factor for diabetic complications." JAMA 295:1707, 2006.

Bruce, D.G., et al. "Physiological importance of deficiency of early prandial insulin secretion in non-insulin-dependent diabetes." Diabetes 37:736-44, 1988.

Bullock BP et al. "Tissue distribution of messenger ribonucleic acid encoding the rat glucagon-like peptide-1 receptor." Endocrinology 137:2968, 1996.

Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.

Calles-Escandon, J. and Robbins, D.C. "Loss of early phase insulin release in humans impairs glucose tolerance and blunts thermic effect of glucose." Diabetes 36:1167-72, 1987.

Camilleri, Clinical Practice: Diabetic Gastroparesis. The New England Journal of Medicine, 356: 820-829 (2007).

Campos et al. "Divergent tissue-specific and developmental expression of receptors for glucagon and glucagon0like peptide-1 in the mouse." Endocrinology 134:2156, 1994.

Cassidy J P, Amin N, Marino M, et al. Insulin lung deposition and clearance following Technosphere® insulin inhalation powder administration. Pharmaceutical Research 2011; 28:2157-2164.

Cassidy J, Amin N, Baughman R, et al. Insulin kinetics following Technosphere® insulin inhalation powder administration unchanged in albuterol-treated asthmatics. ADA 2010; Poster 522.

Cassidy J, Baughman RA, Tonelli G, et al. Use of rapid acting insulin analog as the baseline infusion during glucose clamping improves pharmacokinetic evaluation. ADA 2007; 56: Abstract 602-P.

Cassidy JP, Baughman RA, Schwartz SL, et al. AFRESA® (Technosphere® insulin) dosage strengths are interchangeable ADA 2009; Poster 433.

Cassidy JP, Marino MT, Amin N, et al. Lung deposition and absorption of insulin from AFRESA® (Technosphere® insulin) ADA 2009; Poster 425.

Cassidy JP, Potocka E, Baughman RA, et al. Pharmacokinetic characterization of the Technosphere® inhalation platform Diabetes Technology Meeting 2009. poster.

Caumo et al. "First-phase insulin secretion: does it exist in real life" Considerations on shape and function. Am J Physiol Endocrinol Metab 287:E371-E385, 2004.

Cefalu "Concept, Strategies and Feasibility of Noninvasive Insulin Delivery." Diabetes Care 27:239-246, 2004.

Cefalu "Novel routes of insulin delivery for patients with type 1 or type 2 diabetes." Ann Med 33:579-586, 2001.

Cefalu et al., Inhaled human insulin treatment in patients with type 2 diabetes mellitus. Ann. Int. Med., 2001, 134(3):203-207.

Ceglia et al. "Meta-analysis: efficacy and safety of inhaled insulin therapy in adults with diabetes mellitus." Ann Intern Med 145:665, 2006.

Cerasi, et al. Decreased sensitivity of the pancreatic beta cells to glucose in prediabetic and diabetic subjects. A glucose dose-response study. Diabetes 21(4):224-34, 1972.

Cernea et al. "Dose-response relationship of oral insulin spray in healthy subjects." Diabetes Care 28:1353-1357, 2005.

Cernea et al. "Noninjectable Methods of Insulin Administration." Drugs of Today 2006, 42 (6): 405-424.

Chan et al., "Pharmacological Management of Type 2 Diabetes Mellitus: Rationale for Rational Use of Insulin", Mayo Clin Proc, 2003, 78, 459-467.

Chase et al., "Redefining the clinical remission period in children with type 1 diabetes", Pediatric Diabetes, 2004, 5, 16-19.

Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).

Cheatham et al. "A novel pulmonary insulin formulation replicates first phase insulin release and reduces s-proinsulin levels." Presented at the American Diabetes Association 64th Scientific Sessions, Jun. 2004, abstract 457-P.

Cheatham et al. "Prandial Technosphere®/Insulin inhalation provides significantly better control of meal-related glucose excursions than prandial subcutaneous insulin." Presented at the Diabetes Technology Society meeting, Oct. 2004.

Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.

Chemical Abstracts, vol. No. 114(22), Abstract No. 214519x (1990).

Chemicaland21.com. Solvents. Dec. 12, 2008. Available from: <http://web.archive.org/web20081212035748/http://www.chemicalland21.com/info/SOLVENTS.htm.

Chow et al., Particle Engineering for Pulmonary Drug Delivery. Pharmaceutical Research, vol. 24, No. 3, pp. 411-437 (2007).

Clee et al. Nature Genetics 38:688-693, 2006.

Cobble "Initiating and Intensifying Insulin Therapy for Type 2 Diabetes: Why, When, and How." Am J Ther. Jan. 8, 2009.

Coffey et al. "Valuing heath-related quality of life in diabetes." Diabetes Care 25:2238, 2002.

Colagiuri et al., Are lower fasting plasma glucose levels at diagnosis of type 2 diabetes associated with improved outcomes? Diabetes Care, vol. 25, pp. 1410-1417 (2002).

Combettes and Kargar, C, Newly Approved and Promising Antidiabetic Agents. Therapie, Jul.-Aug. 2007: 62 (4): 293-310.

Coors et al., Polysorbate 80 in medical products and nonimmunologic anaphylactoid reactions. Ann. Allergy Astha Immunol., 95(6): 593-599 (2005).

(56) References Cited

OTHER PUBLICATIONS

Costello et al., "Zinc inhibition of mitochondrial aconitase and its importance in citrate metabolism in prostate epithelial cells", Journ. Biol. Chem. 272(46):28875-28881 (1997).
Cricket TM Single-Use Inhalers [on-line]. MannKind Technologies Website, posted in 2011, [retrieved on Jul. 30, 2012]. Retrieved from the Internet. <URL:mannkindtechnologies,com/DeviceTechnology/CricketSingleUseInhalers.aspx>.
Crosby, J. "Dog Normals", <http://vetmedicine.about.com/od/diseasesconditionsfaqs/tp/TP_dogfacts.htm>, copyright 2013.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., Elimination of the action of glucagon-like peptide 1 causes an impairment of glucose tolerance after nutrient ingestion by healthy baboons. J. Clin. Invest., 97:133-38 (1996).
Database adisinsight, "Gucagon-like peptide-1 inhalation-MannKind Corporation", Database accession No. 2009:1048 Abstract.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria." Lancet. Aug. 21, 1999;354(9179):617-21.
DedicatedPhase, "Preclinical Trials and Research", <http://www.dedicatedphase1.com/preclinical-research.html>, copyright 2006-2011, p. 1.
Definition of analog from http://cancerweb.ncl.ac.uk/omd/about.html, pp. 1-5. Accessed by Examiner on Jul. 7, 2005 and cited in Office Action issued on Jul. 26, 2013 in U.S. Appl. No. 12/830,557.
Del Prato S "Unlocking the opportunity of tight glycemic control" Diabetes Obesity and Metabolism 7:S1-S4, 2005.
Delgado-Aros et al. "Effect of GLP-1 on gastric volume, emptying, maximum volume ingested and postprandial symptoms in humans." Am J Physiol Gastrointest Liver Physiol 282:G424, 2002.
Diabetes: Counting Carbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother., 2003, 4, 191-200.
Dorwald, F.A. Side reactions in organic synthesis. Wiley, (2005).
Doyle et al. "Glucagon-like peptide-1." Recent Prog Horm Res. 2001;56:377-99.
Dreamboat TM Reusable Inhalers [on-line]. MannKind Technologies Website, posted in 2011, Retrieved from the Internet: <URL: mannkindtechnologies.com/Device Technology/Dream Boat Reuseable Inhalers.aspx>.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Drug Delivery, Easing the drug delivery route, Jun. 2006, Pharmaceutical & Medical Packaging News, Canon Communications.
Dungan et al., Glucagon-like peptide 1-based therapies for type 2 diabetes: a focus on exntadtide. Clinical Diabetes, 23: 56-62 (2005).
Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.

Edited by Fukushima, Masanori, "Arterial Sclerosis," Merck Manual 17th, Japanese Edition, Nikkei BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.
Edwards CMB et al. "Subcutaneous glucagon-like peptide-1(7-36) amide is insulinotropic and can cause hypoglycaemia in fasted healthy subjects." Clinical Science 96:719, 1998.
Edwards et al., Recent advances in pulmonary drug delivery using large, porous inhaled particles. Journal of Applied Physiology, pp. 379-385 (1998).
Eggers et al., Molecular confinement influences protein structure and enhances thermal protein stability. Protein Sci., 10:250-261 (2001).
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Exubera indications, dosage, storage, stability. Http://www.rxlist.com/cgi/generic4/exubera_ids.htm, 2008.
Exubera package insert, p. 1, 2008.
Fadl et al., Effects of MDI spray angle on aerosol penetration efficiency through an oral airway cast. Journal of Aerosol Science, vol. 38, No. 8, pp. 853-864 (2007).
Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).
Farr, S.J. et al., Pulmonary insulin administration using the AERx® system:physiological and physiochemical factors influencing insulin effectiveness in healthy fasting subjects. Diabetes Tech. Ther. 2:185-197, 2000.
Fehmann et al. "Cell and molecular biology of the incretin hormones glucagon-like peptide-1 and glucose-dependent insulin releasing polypeptide." Endocrine Reviews 16:390, 1995.
Ferrin et al, Pulmonary retention of ultrafine and fine particles in rats. Am. J. Repir. Cell Mol. Biol., pp. 535-542 (1992).
Festa et al., "LDL particle size in relation to insulin, proinsulin, and insulin sensitivity" Diabetes Care, 22(10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorn Insulin, or Bedtime Insulin Glargine in Patients with Type 2 Diabetes." American College of Physicians 2003.
Galinsky et al., A synthesis of diketopiperazine's using polyphosphoric acid. Journal of the American Pharmaceutical Association, vol. 46, No. 7, pp. 391-393 (1957).
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Garg SK, Kelly W, Freson B, et al. Treat-to-target Technosphere® insulin in patients with type 1 diabetes. ADA 2011; Abstract 941-P.

(56) References Cited

OTHER PUBLICATIONS

Garg SK, McGill JB, Rosenstock J, et al. Technosphere® insulin vs insulin lispro in patients with type 1 diabetes using multiple daily injections. ADA, Abstract 917-P (2011).
Gates BJ "Update on advances in alternative insulin therapy." Advances in Pharmacy 1:159-168, 2003.
Glucagon for Injection (1999) glucagon for injection (rDNA origin), pp. 1-7.
Glucagon-like peptide-1; http://en.wikipedia.org/wiki/Glucagon-like peptide-1 (accessed Apr. 24, 2015).
Glucophage Product Insert. Jan. 2009.
Glucotrol Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like peptide 1-(7-36)-amide receptor of insulin-secreting beta-cells. J. Biol. Chem. 268(26):19650-19655 (1993).
Golpon et al. "Vasorelaxant effect of glucagon-like peptide-(7-36) amide and amylin on the pulmonary circulation of the rat." Regulatory Peptides 102:81, 2001.
Gonzalez et al., Actualizacion del tratamiento farmacologico de la diabetes mellitus tipo 2. Del Sistema Nacional de Salud. vol. 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2006; Poster.
Grant ML, Greene S, Stowell GW, et al. Mimicking endogenous peptide secretion by inhalation APS 2009; poster.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardiovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedom (NPH) Therapy in Newly Diagnosed Type 1 Diabetes." Pediatrics, 121(3), e466-e472, 2008.
Hassan et al. "In vivo dynamic distribution of 131I-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, p. 1343-1347.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. (Original and English translation provided in one document).
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.

(56) References Cited

OTHER PUBLICATIONS

Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data from clinical trials of subjects with type 1 diabetes using prandial inhaled Technosphere® insulin. Diabetologia 2009; 52 (suppl 1).
Howard CP, Gnudi L, Loiter D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Loiter D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R, Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1 diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime AFRESA® (inhaled Technosphere® insulin) and basal insulin versus premixed insulin ADA 2009; Poster 551.
http://www.bilcaresolutions.com/en/products/pharma-packaging-innovations-pvc-aclar-films <URL:http://web.archive.org/web/20110127102552/http://www.bilcaresolutions.com/en/products/pharma-packaging-innovations-pvc-aclar-films> published on Jan. 27, 2011 as per "Wayback Engine".
http://www.pmpnews.com/article/blister-packaging-materials (May 26, 2009).
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.
Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin inhalation NN 1998, Drugs R & D, 2004, pp. 46-49, Adis Data Information BV.
Insulin is a natural product from http://www.levemir.com/startingoninsulin/whatisinulin.aspx, pp. 1-3. Accessed by Examiner on Apr. 30, 2014 and in Non-Final Offfice Action dated May 22, 2014 for U.S. Appl. No. 13/797,657 and in Non-Final Office Action dated May 22, 2014 for U.S. Appl. No. 12/883,369.
International Search Report for PCT International Application No. PCT/US2010/055323 filed on Nov. 3, 2010.
Witten Opinion mailed on Jul. 1, 2013 for International Application No. PCT/US2013/032162 filed on Mar. 15, 2013.
International Search Report mailed on Jun. 21, 2010 for International Application No. PCT/US2010/027038 filed on Mar. 11, 2010.
Witten Opinion for International Application No. PCT/US2011/060057 filed on Nov. 9, 2011.
International Search Report mailed Mar. 18, 2013 for International Application No. PCT/US2012/061749 filed on Oct. 24, 2012.
International Search Report mailed on Jun. 20, 2012 for International Applicaion No. PCT/US2012/031695 filed on Mar. 30, 2012.
International Search Report mailed on Nov. 19, 2014 for International Application No. PCT/US2014/049817 filed on Aug. 5, 2014.
International Search Report for International Application No. PCT/US2010/020448 filed on Jan. 8, 2010.
International Search Report mailed on Mar. 11, 2010 for International Application No. PCT/US2009/069745 filed on Dec. 29, 2009.
International Search Report mailed on Oct. 17, 2011 for International Application No. PCT/US2010/026271 filed on Mar. 4, 2010.
International Search Report for International Application No. PCT/US2010/038287 filed on Jun. 11, 2010.
Ishibashi, Norio et al. "Studies on Flavored Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
International Search Report for International Application No. PCT/US2013/050392 filed on Jul. 12, 2013.
Johnson et al., "Turbuhaler a new device for dry powder terbutaline inhalation", Allergy 43(5):392-395 (1988).
Johnson et al: RyR2 and calpain-10 delineate a novel apoptosis pathway in pancreatic islets. J Biol Chem., 279(23):24794-802, 2004.
Johnson, Keith A., Preparation of peptide and protein powders for inhalation. Advanced Drug Delivery Reviews 1997; 26:3-15.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319-1328, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Nε-(Fumaroyl)diketopiperazine of L-Lys (FDKP) Interactions." Molecular Pharmaceutics, vol. 5, No. 2, 294-315, published on web 2008.

(56) References Cited

OTHER PUBLICATIONS

Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 43:1549-1557, 1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Klinger et al., Insulin-micro and nanoparticles for pulmonary delivery. International Journal of Pharmaceutics, vol. 377, pp. 173-179 (2009).
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Flow Through a Simulated DPI, Chapter 3, pp. 43-56 (2001).
Labiris et al., Pulmonary drug delivery. Part I: Physiological factors affecting therapeutic effectiveness of aerosolized medications. British Journal of Clinical Pharmacology 56: 588-599 (2003).
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Leiner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).
Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Li et al. "GLP-1; a novel zinc finger protein required in somatic cells of the gonad for germ cell development." Dev Biol 301:106, 2007.
Li, Jun. Chapter 15: Drug Therapy of Metabolic Diseases. Clinical Pharmacotherapy, People's Medical Publishing House, 1st Edition, pp. 333-335 (2007).
Lian et al. "A Self-Complimentary Self-Assembling Microsphere System: Application for Intravenous Delivery of the Antiepilpetic and Neuroprotectant Compound Felbanate." J Pharm Sci 89:867-875, 2000.
Lim, "Microencapsulation of Living Cells and Tissues", J. Pharm. Sci., 70: 351-354 (1981).
Linder et al., Increase in serum insulin levels is correlated with lung distribution after pulmonary delivery of Technosphere/Insulin. Diabetologia, No. 46, A277 (2003).
Liu et al., "Pulmonary delivery of free and liposomal insulin", Pharmaceuticals Res. 10:228-232, 1993.
Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.
Luque et al. "Glucagon-like peptide-1 (GLP-1) and glucose metabolism in human myocytes." J. Endocrinol 173:465, 2002.
Luzi, L. and DeFronzo, R.A. "Effect of loss of first-phase insulin secretion on hepatic glucose production and tissue glucose disposal in humans." Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.
Malhotra et al., Exendin-4, a new peptide from Heloderma suspectum venom, potentiates cholecystokinin-induced amylase release from rat pancreatic acini. Regulatory Peptides, 41:149-56, 1992.
Mandal "Inhaled insulin for diabetes mellitus." Am J Health Sys Pharm 62:1359-64, 2005.
Mann "Pulmonary insulin—the future of prandial insulin therapy." Presented at the 5th Annual Meeting of the Diabetes Technology Society, Nov. 2005, abstract A94.
MannKind Corporation "Postprandial hyperglycemia: clinical significance, pathogenesis and treatment." MannKind Corporation Monograph. 2009.

(56) References Cited

OTHER PUBLICATIONS

MannKind Corporation, Pulmonary Delivery: Innovative Technologies Breathing New Life into Inhalable Therapeutics, www.ondrugdelivery.com, 2006.
Burcelin et al., Long-lasting antidiabetic effect of a dipeptidyl peptidase IV-resistant analog of glucagon-like peptide-1. Metabolism, vol. 48, No. 2, pp. 252-258 (1999).
Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.
Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.
Marino MT, Cassidy JP, Smutney CC, et al. Improvement in bioavailability of FDKP and insulin with the NGDSB device. Third International Conference on Advanced Technologies and Treatments for Diabetes 2010; Poster 107.
Marino MT. A pharmacokineticipharmacodynamic model of inhaled insulin with application to clinical trial simulation. ADA 2010; Abstract 2105-PO.
Marino MT. Cassidy JP, Baughman RA, et al. C-peptide correction method to determine exogenous insulin levels in pk studies using AFRESA® (Technosphere® insulin [TI]) ADA 2009; Poster 1451.
Marshall "Preventing and detecting complications of diabetes." BMJ 333:455, 2006.
Mastrandrea "A breath of life for inhaled insulin: severe subcutaneous insulin resistance as an indication." Pediatric Diabetes 2010: 11: 377-379.
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hotmelt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matsui et al. "Hyperplasia of type II pheumocytes in pulmonary lymphangioleiomyomatosis. Immunohistochemical and electron microscope study." Arch Pathol Lab Med 124:1642, 2000.
Matthews DR et al. "Homeostasis model assessment: insulin resistance and beta-cell function from fasting plasma glucose and insulin concentrations in man." Diabetologia. Jul. 1985;28(7):412-9.
McElduff A et al. "Influence of acute upper respiratory tract infection on the absorption of inhaled insulin using the AERx(R) insulin diabetes management system." Br J Clin Pharmacol 59:546, 2005.
McMahon et al., "Effects of basal insulin supplementation on disposition of mixed meal in obese patients with NIDDM", Diabetes, vol. 38, pp. 291-303 (1989).
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mendes et al., A non-dimensional functional relationship for the fine particle fraction produced by dry powder inhalers, Aerosol Science 38, pp. 612-624 (2007).
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Merck Manual 17th, Japanese Edition, Nikkei BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Montrose-Rafizadeh et al., Diabetes, 45(Suppl. 2):152A, 1996.
Moren, Aerosols in Medicine (2nd Ed.), Elsevier, pp. 321-350 (1993).
Mudaliar et al., Insulin Therapy in Type 2 Diabetes. Endocrinology and Metabolism Clinics, vol. 30, No. 4, pp. 1-32 (2001).
Nagai et al., "Powder Dosage Form of Insulin for Nasal Administration", J. Control Ref., 1:15-22 (1984).
Narayan et al. "Impact of recent increase in incidence on future diabetes burden." Diabetes Care 29:2114, 2006.
Naslund E et al. "GLP-1 slows solid gastric emptying and inhibits insulin, glucagon, and PYY release in humans." Am J Physiol (Regulatory Integrative Comp Physiol 46):R910, 1999.
Naslund E et al. "Prandial subcutaneous injections of glucagon-like petide-1 cause weight loss in obese human subjects." Br J Nutrition 91:439, 2004.
International Search Report mailed on Nov. 21, 2013 for International Application No. PCT/US2013/057397 filed on Aug. 29, 2013.
Eavarone et al., A voxel-based monte carlo model of drug release from bulk eroding nanoparticles. Journal of Nanoscience and Nanotechnology, vol. 10, pp. 5903-5907 (2010).
Marino MT, Cassidy JP, Smutney CC, et al. Improvement in bioavailability of FDKP with the NexGen2A device: Implications for delivery of pulmonary insulin. Diabetes Technology Meeting 2009; poster.
Nathan DM et al. "Management of hyperglycemia in Type 2 diabetes: a consensus algorithm for the initiation and adjustment of therapy." Diabetes Care 29:1963-1972, 2006.
Nathan DM et al. "Management of hyperglycemia in Type 2 diabetes: a consensus algorithm for the initiation and adjustment of therapy." Diabetes Care 31:173-175, 2008.
Nathan DM et al. "Management of hyperglycemia in Type 2 diabetes: a consensus algorithm for the initiation and adjustment of therapy." Diabetes Care 32:193-203, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Melllitus" N. Eng. J. Med., 2002, 347, 1342-9.
Nauck "Is glucagon-like peptide 1 an incretin hormone?" Diabetologia 42:373-379, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46-52, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).

(56) References Cited

OTHER PUBLICATIONS

NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.
Oberdorster et al., Correlation between particle size, in vivo particle persistence, and lung injury. Environ Health Perspect 102 Suppl 5, pp. 173-179 (1994).
Oberdorster et al.,Pulmonary effects of inhaled ultrafine particles. International Archives of Occupational and Environmental Health, vol. 74, pp. 1-8 (2001).
Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 64, pp. 373-379 (2007).
Orgsoltab et al., Division of Organic Chemistry. Ohio Northern University. Nov. 24, 2009. Available from: <http://www.2.onu.edu/~b-meyers/organic_solvents.html>.
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, p. 235-247.
Onoue et al., Dry powder inhalation systems for pulmonary delivery of therapeutic peptides and proteins. Expert Opin. Ther. Patents 18(4):429-442 (2008).
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Pesic, Inhaler delivers more drug to the deep lung, says Cambridge Consultants. in-Pharma Technologist.com, http://www//in-pharmatechnologist.com/content/view/print/344335, Dec. 1, 2010.

Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).
Pfeiffer MA et al. Insulin secretion in diabetes mellitus. Am J Med 70:579-88, 1981.
Pfutzner et al., Abstract 812: Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.
Pfutzner A et al. "Pulmonary insulin delivery by means of the Technosphere(TM) drug carrier mechanism." Expert Opin Drug Deliv 2:1097-1106, 2005.
Pfützner A et al. "Technosphere®/Insulin—a new approach for effective delivery of human insulin via the pulmonary route." Diab Tech Ther 4:589-594, 2002.
Pfützner A et al. "Lung distribution of radiolabeled Technosphere™/Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potocka E, Baughman R A, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAPS Journal. 2009; 11(S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.

(56) References Cited

OTHER PUBLICATIONS

Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. AFRESA™ supresses endogenous glucose production earlier than a rapid-acting analog (Lispro) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Laube et al., The lung as an alternative route for delivery for insulin in controlling postrprandial glucose levels in patients with diabetes. Chest, Preliminary Report 114 (6) : 1734-1739 (1998).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, *Streptomyces* sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Phillips M, Amin N, et al. Hypoglycemia in patients with type 1 diabetes incorporating prandial inhaled Technosphere® insulin into their usual diabetes treatment regimen vs continuing their usual diabetes management. AACE 2010; Poster 283.
Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.
Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).
Raufman et al., Truncated glucagon-like peptide-1 interacts with exendin receptors on dispersed acini from guina pig pancreas. J. Biol. Chem. 267(30) : 21432-21437 (1992).
Raun et al. "Liraglutide, a long-acting glucagon-like peptide-1 analog, reduces body weight and food intake in obese candy-fed rats, where as a dipenptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Dose Response of Inhaled Dry-Powder Insulin and Dose Equivalence to Subcutaneous Insulin Lispro." Diabetes Care 28:2400-2405, 2005.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Results of a Dose-Response Study with a New Pulmonary Insulin Formulation and Inhaler." Diabetes 49, Supplement, May 2000, A75.
Rave et al. "Time-action profile of inhaled insulin in comparison with subcutaneously injected insulin lispro and regular human insulin." Diabetes Care 28:1077, 2005.
Rave K, Heise T, Pfuetzner A, et al. Assessment of dose-response characteristics for a new pulmonary insulin formulation and inhaler. Exp Clin Endocrinol Diabetes 2000; 108:S161.
Rave K, Potocka E, Boss AH, et al. Pharmacokinetics and linear exposure of AFRESA™ compared with the subcutaneous injection of regular human insulin Diabetes, Obesity and Metabolism 2009; 11:715-720.
Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.
Razavi et al. "TRPVI+ sensory neurons control beta cell stress and islet inflammation in autoimmune disease." Cell 127:1123, 2006.
Retrieved from website: http://groups.molbiosci.northwestern.edu/holmgren/Glossary/Definitions/Def-P/placebo.html, 1 page, Retrieved on Mar. 12, 2013.
Rhodes et al. "Technosphere: Microspherical Particles from Substituted Diketopiperazines for Use in Oral Drug Delivery." 208th ACS National Meeting, Aug. 1994.
Richardson et al. "Technosphere Insulin Technology." Diabetes Technology & Therapeutics, vol. 9, Supplement 1, pp. S65-S72, 2007.
Richardson PC, Potocka E, Baughman RA, et al. Pharmacokinetics of Technosphere® insulin unchanged in patients with chronic obstructive pulmonary disease. Diabetologia 2009; 52 (suppl 1).
Richter et al. "Characterization of glucagon-like peptide-1(7-36)amide receptors at rat membranes by covalent cross-linking." FEBS Letters 280:247, 1991.
Richter et al. "Characterization of receptors for glucagon-like peptide-1 (7-36)amide on rat lung membranes." FEBS Letters 267:78, 1990.
Riddle "Combining Sulfonylureas and Other Oral Agents." Am J Med, 2000, vol. 108(6A), pp. 15S-22S.
Riddle et al. "Emerging therapies mimicking the effects of amylin and glucagon-like peptide 1." Diabetes Care 29:435, 2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosen et al., Substance P microinjected into the periaqueductal gray matter induces antinociception and is released folliong morphine administration. Brain Research, 1001: 87-94 (2004).
Rosenmund et al., Diketopiperazines from Leuchs Anhydrides. Angew Chem Intern. Edit. vol. , No. 2 (1970).
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.
Rosenstock et al. "Inhaled Insulin Improves Glycemic Control when Substituted for or Added to Oral Combination Therapy in Type 2 Diabetes." Ann Intern Med 143:549-558, 2005.

(56) References Cited

OTHER PUBLICATIONS

Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.
Rossiter A, Amin N, Harris R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Roumeliotis, New inhaler launched with a bag, in-Pharma Technologist.com, Decision News Media SAS (2006).
Rousseau et al. "Drug delivery by fumaryl diketopiperazine particles: evidence for passive transport." Presented at be American Diabetes Association 64th Scientific Sessions, Jun. 2004, abstract 484-P.
Rubin RR, Peyrot M. Psychometric properties of an instrument for assessing the experience of patients treated with inhaled insulin: The inhaled insulin treatment questionnaire (INTQ) Health & Quality of Life Outcomes Aug. 2010:32.
Rubin RR, Peyrot M; Patient reported outcomes in adults with type 1 diabetes using mealtime AFRESA® (inhaled Technosphere® insulin) or rapid acting insulin with basal insulin ADA 2009; Poster 1881.
Ryan EA et al. "Successful islet transplantation. Continued insulin reserve provides long-term glycemic control." Diabetes 51:2148-2157, 2002.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney et al., Bioerodible hydrogels based on photopolymerized poly(ethylene glycol)-co-poly(a-hydroxy acid) diacrylate macromers. Macromolecules, 26: 581-587 (1993).
Schaffer et al. "Assembly of high-affinity insulin receptor agonists and antagonists from peptide building blocks." PNAS 100:4435-4439, 2003.
Schepp et al., Eur. J. Pharmacol., 269:183-91, 1994.
Scherbaum "Unlocking the opportunity of tight glycaemic control. Inhaled insulin: clinical efficacy." Diabetes Obesity and Metabolism 7:S9-S13, 2005.
Schirra et al. "Gastric emptying and release of incretin hormones after glucose ingestion in humans." J Clin Invest 97:92-103, 1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen activator inhibitor type 1 in endothelial cells", Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254-1258, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying. J. Gene Medicine 2002; 4:428-437.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shimada et al. Translocation pathway of the intertracheally instilled ultrafine particles from the lung into the blood circulation in the mouse. Toxicologic Pathology pp. 949-957 (2006).
Shojania et al. "Effect of quality improvement strategies for type 2 diabetes on glycemic control." JAMA 296:427, 2006.
Silverstein et al., "Care of Children and Adolescens with Type 1 Diabetes, a Statement of the American Diabetes Association", Diabetes Care, Jan. 2005, vol. 28, p. 186-212.
Singh et al., Use of 125I-[Y39]exendin-4 to characterize exendin receptors on dispersed pancreatic acini and gastric chief cells from guinea pig. Regul. Pept. 53 : 47-59 (1994).
Simms JR, Carballo I, Auge CR, et al. Assessment of immunotoxic effects on humoral and cellular immune parameters following repeated inhalation of Technosphere insulin in the rat. Diabetes 2005;54:Abstract 2078-PO.
Skyler, Pulmonary insulin: current status. Diabetes Voice, vol. 51, Issue I, p. 23-25, 2006.
Skyler "Pulmonary Insulin Delivery—State of the Art 2007" Diabetes Tecnology & Therapeutics, vol. 9, Supplement 1, pp. S1-S3. 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardio-vascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3. Accessed by Examiner on May 16, 2014 and in Non-Final Offfice Action dated

(56) References Cited

OTHER PUBLICATIONS

May 22, 2014 for U.S. Appl. No. 13/797,657 and in Non-Final Office Action dated May 22, 2014 for U.S. Appl. No. 12/883,369.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere®/Insulin." Diabetes 49 Supplement, May 2000, A126.
Steiner et al. "Technosphere®, a novel drug delivery system for oral administration of calcitonin." Pharmaceutical Res 11:S299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technosphere™/insulin. Exp Clin Endocrinol Diabetes 2000; 108:S161.
Steiner S, Rave K, Heise T, et al. Technosphere™/insulin: Bioavailability and pharmacokinetic properties in healthy volunteers. Diabetologia 2000;43:Abstract 511-P.
Steiner SS, Burrell BB, Feldstein R, et al. Pulmonary delivery of Technosphere™/insulin: Increased bioefficacy and bioavailability in clinical trials using the PDC Medtone™ inhaler. Proceed Int'l Symp Control Rel Bioact Mater 2000; 27: 1000-1001.
Stowell et al. "Development of GLP-1 Technosphere(TM) powder: an inhaled GLP-1 product." Diabetes Technology Meeting, San Francisco, Oct. 2007.
Strack "Inhaled Human Insulin." Drugs of Today 2006, 42 (4): 207-221.
Sturis et al., GLP-1 deriative liraglutide in rats with beta-cell deficiences: influence of metabolic state on beta-cell mass dynamics. British Journal of Pharmacology, 140 : 123-132 (2003).
Svartengren et al., Added External Resistance Reduces Oropharyngeal Deposition and Increases Lung Deposition of Aerosol Particles in Asthmatics. Am. J. Respir. Crit. Care Med., vol. 152, pp. 32-37, 1995.
Sympatecs. Dry Dispersion for Laser Diffraction and Image Analysis, 2011. XP-002586530.
Leone-Bay et al., Innovation in drug delivery by inhalation. Ondrugdelivery, No. 7, pp. 4-8 (2010).
Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.
Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008; 2(1) :47-57.
Tang-Christensen et al. "Central administration of GLP-1-(7-36) amide inhibits food and water intake in rats." Am J Physiol 271 (Regulatory Integrative Comp Physiol 40):R848, 1996.
Taylor et al. "Aerosols for macromolecule delivery. Design challenges and solutions." Am J Drug Deliv 2:143-155, 2004.
Teeter et al. "Dissociation of lung function changes with humoral immunity during inhaled human insulin therapy." Am J Resp Crit Care Med 173:1194, 2006.
Telko et al., Dry Powder Inhaler Formulation. Respiratory Care, Sep. 2005, vol. 50, No. 9, 1209-1227.
The American Diabetes Association "Insulin Administration" Diabetes Care, vol. 27, Supplement 1, S106-S109 (2004).
Gerber et al., Treatment satisfaction with inhaled insulin in patients with type 1 diabetes. Diabetes Care 24:1556-1559 (2001).
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens B et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in non-insulin-dependent diabetes mellitus." Eur J Clin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.
Triantafyllidis et al., Structural, compositional and acidic characteristics of nanosized amorphous or partially crystalline ZSM-5 zeolite based materials. Microporous and Mesoporous Materials, 75:89-100 (2004).
Tu N, Kramer DA, Baughman RA. Inhaled Technosphere® Insulin improves glycemic control without weight gain. Diabetes 2007;56:Abstract 471-P.
Tuley et al., Experimental observations of dry powder inhaler dose fluidisation. International Journal of Pharmaceutics, 358, pp. 238-247 (2007).
Utah Valley University. Saponification. © 2009. Available from: <http://science.uvu.edu/ochem/index.php/alphabetical/s-t/saponification/printpage/>.
Vaczek, Accelerating drug delivery firms exploring new drug-delivery routes and devices intently awaiting the commmercial launch of Exubera. Pharmaceutical & Medical Packaging News, vol. 14, No. 6 (2006).
Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.
Van Alfen-Van Der Velden et al. "Successful treatment of severe subcutaneou insulin resistance with inhaled insulin therapy", Pediatric Diabetes 2010: 11:380-382.
Vara E et al. "Glucagon-like peptide-1 (7-36) amide stimulates surfactant secretion in human type II pneumocytes." Am J Resp Crit Care Med 163:840-846, 2001.
Vella A et al. "Effect of glucagon-like peptide 1(7-36) amide on glucose effectiveness and insulin action in people with type 2 diabetes." Diabetes 49:611, 2000.
Vella A et al. "The gastrointestinal tract and glucose tolerance." Curr Opin Clin Nutr Metab Care 7:479, 2004.
Vendrame et al. "Prediabetes: prediction and prevention trials." Endocrinol Metab Clin N Am, 2004, vol. 33, pp. 75-92.
Verdich C, et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.

(56) References Cited

OTHER PUBLICATIONS

Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Amorij et al., Development of stable infleunza vaccine powder formulations challenges and possibilities. Pharmaceutical Research, vol. 25, No. 6, pp. 1256-1273 (2008).
Audouy et al., Development of a dried influenza whole inactivated virus vaccine for pulmonary immunization. Vaccine, vol. 29, pp. 4345-4352 (2011).
Volund "Conversion of insulin units to SI units." American Journal of Clinical Nutrition, Nov. 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat. J. Clin. Invest., 95 : 417-421 (1995).
Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines in 2012, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Weissberger, "Mannkind: Overlooked Biotech with Excellent Prospects (Part V)," http://www.investorvillage.com/smbd.asp?mb=28858,mn=45817&pt=msg&mid=5021385 (posted on Jun. 19, 2008, accessed on Oct. 18, 2012).
West, Solid State Chemistry and its Applications, Chp 10, Solid Solutions. Wiley, New York, 358 (1998).
Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.
Witchert, Low molecular weight PLA: A suitable polymer for pulmonary administered microparticles. J. Microencapsulation, 10(2): 195-207 (1993).

Wright et al., Inhaled Insulin: Breathing new life into diabetes therapy. Nursing, vol. 37, No. 1, p. 46-48 (2007).
Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11):4542-4546 (2007).
Yoshida et al., Absorption of insulin delivered to rabbit trachea using aerosol dosage form. J. Pharm. Sci. 68(5):670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Wasada, Glucagon-like peptide-1 (GLP-1). Nihon Rinsho, vol. 62, No. 6, pp. 1175-1180 (2004) (full Japanese article with English abstract).
Bosquillon et al., Pulmonary delivery of growth hormone using dry powders and visualization of its local fate in rates. Journal of Controlled Release 96: 233-244 (2004).
Cho et al., Targeting the glucagon receptor family for diabetes and obesity therapy. Pharmacology & Therapeutics 135: 247-278 (2012).
Definition of medicament from http://medical-dictionary.thefreedictionary.com/medicament, retrieved by the Examiner on Mar. 20, 2015 and cited in Office Action issued on Mar. 26, 2015 in U.S. Appl. No. 13/942,482.
Definition of matrix from http://medical-dictionary.thefreedictionary.com/matrix, retrieved by the Examiner on Mar. 5, 2015 and cited in Office Action issued on Mar. 26, 2015 in U.S. Appl. No. 12/471,260.
Diabetes Frontier, vol. 10, No. 5, p. 647-657 (1999) (full Japanese article with translated English portion provided in separate attachment, portion translated in English is the bottom of p. 655 and the left column of p. 656).
Ely et al., Effervescent dry powder for respiratory drug delivery. European Journal of Pharmaceutics and Biopharmaceutics 65: 346-353 (2007).
European Search report for European Application 14192154.4 mailed on Mar. 19, 2015.
Extended European Search report for European Application 14187552.6 mailed on Mar. 2, 2015.
Gillespie et al., Using carbohydrate counting in diabetes clinical practice. Journal of the American Diabetic Association, vol. 98, No. 8, p. 897-905 (1998).
Yamamoto et al., Engineering of Poly (DL-lactic-co-glycolic acid) Nano-composite particle for dry powder inhalation dosage forms of insulin with spray fluidized bed granulating system. J. Soc. Powder Technol., Japan, 41: 514-521 (2004).

(56) References Cited

OTHER PUBLICATIONS

Shields, Irritable bowel syndrome, archived Jun. 21, 2009, available at: https://web.archive.org/web/200906211 00502/http://www.gastroenterologistpaloalto.com/conditions-diseases-irritable-bowelsyndrome-palo-alto-ca. html; on Aug. 26, 2015 is U.S. Appl. No. 14/139,714.

Smith et al., Evaluation of novel aerosol formulations designed for mucosal vaccination against infleunza virus. Vacine, vol. 21, pp. 2805-2812 (2003).
U.S. Appl. No. 14/873,041, filed Oct. 1, 2015.
Design U.S. Appl. No. 29/504,212, filed Oct. 2, 2014.
U.S. Appl. No. 14/774,311, filed Sep. 10, 2015.
Young et al., Encapsulation of lysozyme in a biodegradable polymer by preparation with a vapor-over-liquid antisolvent. Journal of Pharmaceutical Sciences, 88:640-650 (1999).
Hazard Prevention and Control in the Work Environment: Airborne Dust WHO/SDE/OEH/99. 14 Chapter 1—Dust: Definitions and Concepts [retrieved from internet by Examiner in European case on Sep. 22, 2015]. <URL: http://www.who.int/occupational_health/publications/airdust/en/> published on Oct. 29, 2004 as per Wayback Machine.
Owens et al., Blood glucose self-monitoring in type 1 and type 2 diabetes: reaching a multidisciplinary consensus. Diabetes and Primary Care, vol. 6, No. 1, pp. 8-16 (2004).
U.S. Appl. No. 14/863,136, filed Sep. 23, 2015.
U.S. Appl. No. 14/991,777, filed Jan. 8, 2016.
U.S. Appl. No. 14/971,785, filed Dec. 16, 2015.
U.S. Appl. No. 14/945,168, filed Nov. 18, 2015.
Amodeo et al., Pain peptides. Solution structure of orphanin FQ2. FEBS Letters, vol. 473, Issue 2, pp. 157-160 (2000).
Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).
Krondahl et al., Regional differences in bioavailability of an opioid tetrapeptide in vivo rats after administration to the respiratory tract. Peptides, vol. 23, No. 3, pp. 479-488 (2002).
Lee et al., Intrapulmonary potential of polyethylene glycol-modified glucagon-like peptide-1s as a type 2 anti-diabetic agent. Regulatory Peptides, 152:101-107 (2009).
Selam, Jean-Louis. Inhaled Insulin: Promises and Concerns. Journal of Diabetes Science and Technology, vol. 2, Issue 2, pp. 311-315 (2008).

* cited by examiner

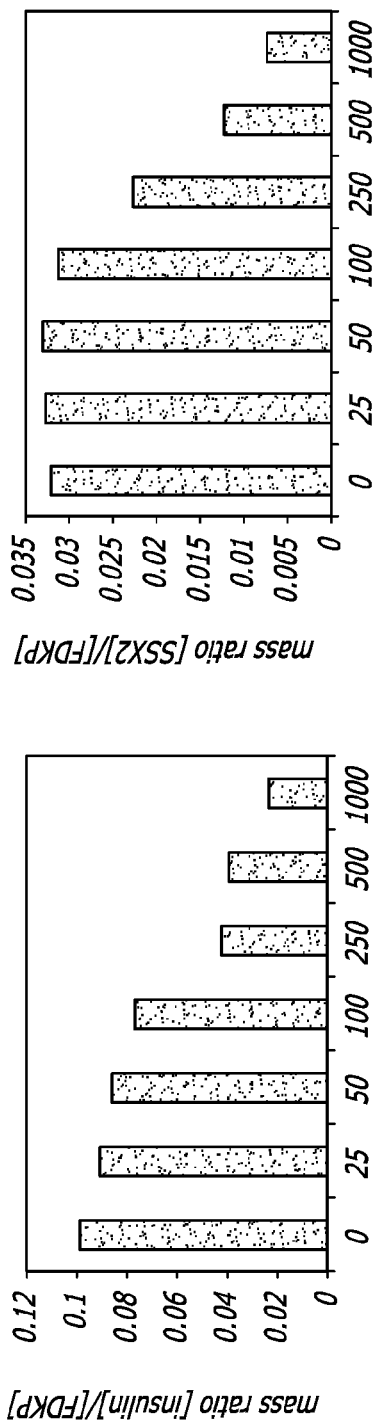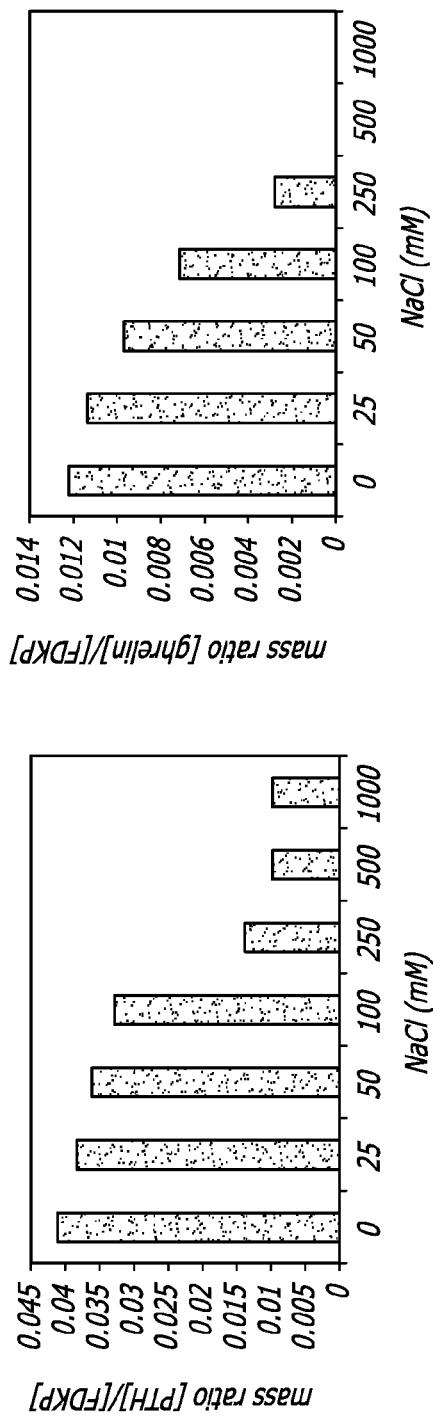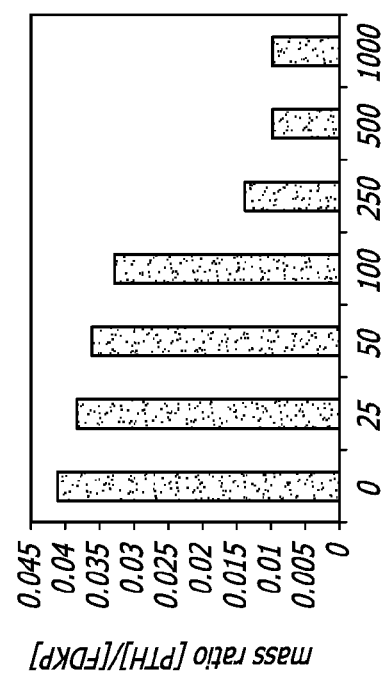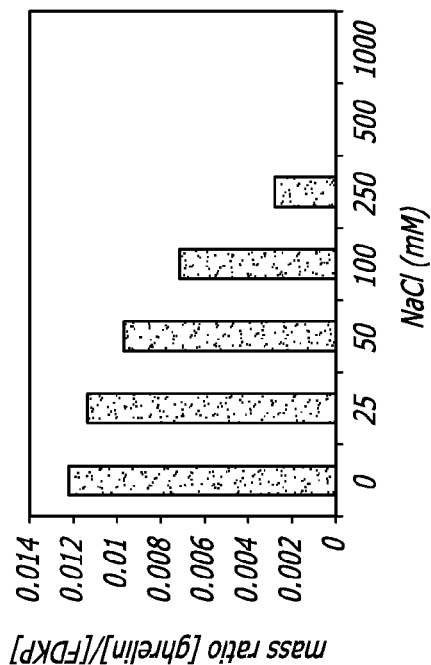

METHOD OF DRUG FORMULATION BASED ON INCREASING THE AFFINITY OF CRYSTALLINE MICROPARTICLE SURFACES FOR ACTIVE AGENTS

CROSS REFERENCE TO RELATED APPLICATIONS

The present application is a divisional application of U.S. patent application Ser. No. 14/249,621, filed Apr. 10, 2014, which is a continuation of U.S. patent application Ser. No. 12/830,557 (now U.S. Pat. No. 8,729,019), filed Jul. 6, 2010, which is a continuation of U.S. patent application Ser. No. 11/532,063 (now U.S. Pat. No. 7,799,344), filed Sep. 14, 2006, which claims the benefit under 35 U.S.C. §119(e) to U.S. Provisional Application Ser. Nos. 60/717,524—filed Sep. 14, 2005—and 60/744,882—filed Apr. 14, 2006—the entire contents of all of which are hereby incorporated by reference in their entirety.

FIELD OF THE INVENTION

This invention is generally in the area of drug formulations and is particularly related to methods of coating active agents onto the surface of crystalline microparticles.

BACKGROUND OF THE INVENTION

Delivery of therapeutic agents has been a major problem. Oral administration is one of the most common and preferred routes of delivery due to ease of administration, patient compliance, and decreased cost. However, the disadvantages of this route include low or variable potency and inefficient adsorption of the therapeutic. This is particularly evident when the compound to be delivered is unstable under conditions encountered in the gastrointestinal tract. A variety of coatings and encapsulation methods have been developed in the art, but only a few are effective in addressing this issue. Still, there are therapeutic compounds that tend to be less active in the conditions of the gastrointestinal tract and must be administered in higher dosages to be adsorbed into the bloodstream in an effective amount.

A broad range of drug formulation systems have been developed to address the problem of optimal drug delivery and are based on incorporation of drug into a matrix that acts as a carrier. Factors considered in drug formulation include requirements that the system be non-toxic, non-reactive with the drug to be delivered, economical to manufacture, formed of readily available components, and consistent with respect to final composition and physical characteristics, including stability and release rate. It is also preferable that the drug delivery system is formed of materials easily removed from the body by normal physiologic processes.

Microparticle drug formulations can be used in numerous routes of administration, but are particularly well suited to pulmonary delivery. Advantages of the lungs for delivery of agents having systemic effects include the large amount of surface area and ease of uptake by the mucosal surface. U.S. Pat. No. 6,071,497, herein incorporated by reference, describes a pulmonary drug delivery system based on the formation of diketopiperazine microparticles as well as polymer-based microparticles.

SUMMARY OF THE INVENTION

Methods are provided for forming a coating of active agent on crystalline microparticles. In general, microparticles are coated with an active agent by modifying the surface properties of the microparticles such that the active agent has a higher affinity for the microparticle surface than for remaining in solution.

The present invention to provide improved methods for coating crystalline particles such as fumaryl diketopiperazine (FDKP) microparticles with active agents, such as proteins, using electrostatically, hydrophobically, or hydrogen-bond driven associations. In the present invention, liquid can optionally be removed (for recovery of active agent coated microparticles) by filtration or drying, or replaced by exchanging for a different solution medium. In any case, removal of the liquid medium is not an obligatory step in formation of the active agent-microparticle complex. This invention discloses a method for microparticle coating based on changing the surface properties of the crystalline microparticles to achieve adsorption of active agent to the microparticle.

In particular embodiments of the present invention, there is provided a method of coating a preformed crystalline microparticle in suspension with an active agent comprising; i) adjusting the energetic interaction between the active agent and the crystalline microparticle independent of solvent removal; and ii) allowing time for the active agent to adsorb onto the surface of the microparticle. In some embodiments, the method of coating a preformed crystalline microparticle in suspension with an active agent can further comprise a step of removing or exchanging the solvent without substantial effect on the interaction between active agent and microparticle.

In other particular embodiments of the present invention, the method of coating the microparticle with active agent is accomplished by modifying the surface properties of the microparticle. Modification of the surface properties of the microparticle is achieved by altering solution conditions. These conditions, in a non-limiting manner, comprise changing the pH. In other embodiments of the invention, the surface properties of the microparticle are modified by: 1) altering the polarity of the solution; 2) the addition of monovalent or multivalent ions; and 3) chemical derivatization of the microparticle.

In yet another embodiment, the present invention further comprises a step of dissolving the active agent in the fluid phase of the suspension of microparticles and subsequently changing the pH. Such step of dissolving the active agent in a fluid phase refers to the dissolving of a solid. In addition, such step of dissolving the active agent refers to the addition of a more concentrated solution of the active agent in addition to adding solid.

In still yet another embodiment, the pH conditions of the microparticle suspension are altered to favor interactions between active agent and microparticle prior to, or after, the addition of active agent.

In other embodiments, the active agent has more than one type of energetically favorable interaction with the microparticle surface.

In another particular embodiment of the present invention, the active agent is insulin or an analog thereof.

In other particular embodiments of the present invention, the surface properties that create a favorable interaction between the active agent and microparticle are selected from the group consisting of electrostatic properties, hydrophobic properties, and hydrogen bonding properties.

In another embodiment of the present invention, the microparticle is porous and has interior surfaces accessible to the bulk fluid of the solution. In one embodiment, the microparticle comprises a diketopiperazine such as fumaryl diketopiperazine but is not limited to such.

In embodiments of the present invention, the method of coating produces a monolayer of active agent on the microparticle surface. In other embodiments of the invention, the monolayer is continuous. In other embodiments of the invention, the active agent in the monolayer can have a preferred orientation.

In yet another embodiment, a method is provided for coating a pre-formed crystalline microparticle in suspension with insulin comprising adjusting the energetic interaction between the active agent and the crystalline microparticle independent of solvent removal; and absorbing the insulin onto the surface of the microparticles.

Solvent, as used herein, refers to the fluid medium in which the active agent and microparticle are "bathed." It should not be interpreted to require that all components are in solution. Indeed in many instances it may be used to refer to the liquid medium in which the microparticles are suspended.

BRIEF DESCRIPTION OF THE DRAWINGS

The following drawings form part of the present specification and are included to further demonstrate certain aspects of the examples disclosed herein. The invention may be better understood by reference to one or more of these drawings in combination with the detailed description of specific embodiments presented herein.

FIG. 1 depicts the ultrasonic HCl titration profiles for separate components of fumaryl diketopiperazine (FDKP) suspension, FDKP particles and buffer, according to the teachings of the present invention. The magnitude of the changes in ultrasonic velocity titration profile (FIG. 1; Panel A) reflects hydration changes caused by protonation of ionizable carboxylate groups of the sample components. The excess ultrasonic attenuation peaks (FIG. 1; Panel B) result from fast relaxation in the proton exchange reaction at the point of saturation. Frequency (F) is 15 MHz, temperature is 25° C.

FIG. 2 depicts the ultrasonic glacial acetic acid titration profiles for FDKP particles+insulin and FDKP particles alone according to the teachings of the present invention. The ultrasonic velocity profile was calculated by subtracting the insulin contribution; frequency is 8 MHz, temperature is 25° C. Excess ultrasonic attenuation as a function of the concentration of glacial acetic acid added is also depicted. Two stages of glacial acetic acid induced acidification are similar to that observed by HCl titration. The inset panel on the left (Panel A) depicts the association of the active agent with the FDKP microparticle at pH greater than about 2.9. The inset panel on the right (Panel B) depicts the reduced interaction between the active agent and the microparticle at pH below about 2.9.

FIG. 3 depicts protein adsorption onto ionizable microparticles according to the teachings of the present invention. Protein was added to the microparticle suspension after pH adjustment, unbound protein was filtered away and the microparticles dissolved to release bound protein.

FIGS. 4A-D depict the pH dependence for the adsorption of active agents onto FDKP microparticles according to the teachings of the present invention. FIG. 4A depicts insulin adsorption; FIG. 4B depicts anti-SSX-$2_{41-49}$ monoclonal antibody adsorption, FIG. 4C depicts parathyroid hormone (PTH) adsorption and FIG. 4D depicts ghrelin adsorption.

FIG. 5 depicts the pH dependence of insulin adsorption onto FDKP microparticles with limiting insulin concentration according to the teachings of the present invention.

FIG. 6 depicts the change in ultrasonic velocity in FDKP microparticle suspension (11 mg/mL) upon stepwise titration of FDKP microparticles with protein (10 mg/mL) according to the teachings of the present invention. The contribution of free protein and the effect of FDKP microparticle dilution were subtracted. Temperature is 25° C.

FIGS. 7A-D depict the saturation curves for adsorption of the active agent onto FDKP microparticles according to the teachings of the present invention. Loading curves are shown for active agent/FDKP microparticles as a function of active agent concentration at pH 5.0. FIG. 7A depicts glucagon-like peptide 1 (GLP-1) adsorption; FIG. 7B depicts PTH adsorption; FIG. 7C depicts anti-SSX$2_{41-49}$ monoclonal antibody adsorption and FIG. 7D depicts anti-MOPC-21 monoclonal antibody adsorption.

FIGS. 8A-D depict adsorption of active agents onto microparticles at pH 5.0 as influenced by increasing concentrations of salt according to the teachings of the present invention. The active agent was added to the microparticle suspension after pH adjustment, unbound agent was filtered away and the microparticles dissolved to release bound agent. FIG. 8A depicts insulin adsorption, FIG. 8B depicts anti-SSX-$2_{41-49}$ monoclonal antibody adsorption, FIG. 8C depicts PTH adsorption and FIG. 8D depicts ghrelin adsorption.

DETAILED DESCRIPTION OF THE INVENTION

Agents to be Delivered

The substance to be coated onto the crystalline microparticle is referred to herein as the active agent. Examples of classes of active agent include pharmaceutical compositions, synthetic compounds, and organic macromolecules that have therapeutic, prophylactic, and/or diagnostic utility.

Generally, any form of active agent can be coated onto the surface of a crystalline microparticle. These materials can be organic macromolecules including nucleic acids, synthetic organic compounds, polypeptides, peptides, proteins, polysaccharides and other sugars, and lipids. Peptides, proteins, and polypeptides are all chains of amino acids linked by peptide bonds. Peptides are generally considered to be less than 30 amino acid residues, but may include more. Proteins are polymers that can contain more than 30 amino acid residues. The term polypeptide as is know in the art and as used herein, can refer to a peptide, a protein, or any other chain of amino acids of any length containing multiple peptide bonds, though generally containing at least 10 amino acids. The active agents used in the coating formulation can fall under a variety of biological activity classes, such as vasoactive agents, neuroactive agents, hormones, anticoagulants, immunomodulating agents, cytotoxic agents, antibiotics, antiviral agents, antigens, and antibodies. More particularly, active agents may include, in a non-limiting manner, insulin and analogs thereof, growth hormone, parathyroid hormone (PTH), ghrelin, granulocyte macrophage colony stimulating factor (GM-CSF), glucagon-like peptide 1 (GLP-1), Texas Red, alkynes, cyclosporins, clopiogrel and PPACK (D-phenylalanyl-L-prolyl-L-arginine chloromethyl ketone), antibodies and fragments thereof, including, but not limited to, humanized or chimeric antibodies; F(ab), $F(ab)_2$, or single-chain antibody alone or fused to other polypeptides; therapeutic or diagnostic monoclonal antibodies to cancer antigens, cytokines, infectious agents, inflammatory mediators, hormones, and cell surface antigens. Non-limiting examples of antibodies to tumor antigens include anti-SSX-2$_{41-49}$ (synovial sarcoma, X breakpoint 2), anti-NY-ESO-1 (esophageal tumor associated antigen), anti-PRAME (preferentially expressed antigen of melanoma), anti-PSMA (prostate-specific membrane antigen), anti-Melan-A (melanoma tumor associated antigen), anti-tyrosinase (melanoma tumor associated antigen), and anti-MOPC-21 (myeloma plasma-cell protein).

Delivery System-Crystalline Microparticles

Essentially, the term "microparticle" refers to a particle with a diameter of about 0.5-1000 µm, irrespective of the precise exterior or interior structure. Within the broad category of microparticles, "microspheres" refers to microparticles with uniform spherical shape. Crystalline microparticles as used herein refers to microparticles that have the internal structure though not necessarily the external form of a crystal and have a regular arrangement of atoms in a space lattice. Ionizable crystalline surfaces refer to crystalline microparticles that have the additional capacity to carry an electrical charge.

Preferably, the chemical substance composing the crystalline microparticle is reversibly reactive with the active agent to be delivered, as well as non-toxic and not metabolized, at least by rodents and humans. In addition, the crystalline structure of preferred microparticles is not substantially disrupted in the process of coating with active agent. The composition of the crystalline microparticle determines what type of chemical interactions can be manipulated to drive adsorption of an active agent to the microparticle surface.

A number of substances can be used to form crystalline microparticles. Microparticles as such have an outer surface, the properties of which can be manipulated in the coating process. Representative materials from which crystalline microparticles can be formed include but are not limited to: aromatic amino acids, salts with limited solubility in a defined pH range such as diketopiperazines and morpholine sulfates.

U.S. Pat. Nos. 5,352,461 and 5,503,852, herein incorporated by reference in their entirety, describe a drug delivery system based on formation of diketopiperazine (DKP) microparticles from diketopiperazine derivatives such as 3,6-bis[N-fumaryl-N-(n-butyl)amino] (also referred to as fumaryl diketopiperazine or FDKP; also termed (E)-3,6-bis[4-(N-carboxy-2-propenyl)amidobutyl]-2,5-diketopiperazine) that are stable at low pH and dissolve at the pH of blood or the small intestine. As disclosed in the above patents, the drug to be delivered is combined or loaded with the diketopiperazine particles by forming DKP microparticles in the presence of drug (payload). A system based on diketopiperazine structural elements, or one of its substitution derivatives, including, but not limited to, diketomorpholines and diketodioxanes, forms microparticles with desirable size distributions and pH ranges as well as good payload tolerance. A wide range of stable, reproducible characteristics can be generated with appropriate manipulations of the substituent groups.

Other diketopiperazines that may be contemplated in the present invention may include 3,6-di(4-aminobutyl)-2,5-diketopiperazine; 3,6-di(succinyl-4-aminobutyl)-2,5-diketopiperazine (succinyl diketopiperazine or SDKP); 3,6-di(maleyl-4-aminobutyl)-2,5-diketopiperazine; 3,6-di(citraconyl-4-aminobutyl)-2-5-diketopiperazine; 3,6-di(glutaryl-4-aminobutyl)-2,5-diketopiperazine; 3,6-di(malonyl-4-aminobutyl)-2,5-diketopiperazine; 3,6-di(oxalyl-4-aminobutyl)-2,5-diketopiperazine and derivatives therefrom. Diketopiperazine salts may also be utilized in the present invention and may included, for example, a pharmaceutically acceptable salt such as the Na, K, Li, Mg, Ca, ammonium, or mono-, di- or tri-alkylammonium (as derived from triethylamine, butylamine, diethanolamine, triethanolamine, or pyridines, and the like). The salt may be a mono-, di-, or mixed salt. Higher order salts are also contemplated for diketopiperazines in which the R groups contain more than one acid group. In other aspects of the invention, a basic form of the agent may be mixed with the diketopiperazine in order to form a drug salt of the diketopiperazine, such that the drug is the counter cation of the diketopiperazine.

U.S. Pat. Nos. 6,444,226, and 6,652,885, each herein incorporated by reference in their entirety, describes preparing and providing microparticles of DKP in aqueous suspension to which a solution of active agent is added, and then the critical step of lyophilizing the suspension to yield microparticles having a coating of active agent. The basis for this formulation is that the coating of microparticle with active agent is driven by removal of the liquid medium by lyophilization. (See also U.S. Pat. No. 6,440,463 which is incorporated herein by reference in its entirety). In contrast to teachings in the prior art, the present invention provides means for adjusting the association of active agent with the microparticle prior to solvent removal. Thus, removal of the liquid medium by bulk physical methods (e.g., filtration or sedimentation) or evaporative methods (e.g., lyophilization or spray-drying) can result in comparable loads.

Controlled Coating of Crystalline Microparticles

Controlled coating refers to the directed process of adsorbing active agent onto the surface of a crystalline microparticle. The coating process involves changing the surface properties of crystalline microparticles in a fluid suspension either by changing solution conditions (such as pH, temperature, polarity, ionic strength, and co-solvents), by complexation to mono- or multi-valent ions, or by chemical derivatization. Altering the surface properties of the microparticle either before or after addition of active agent affects its chemical interactions with active agent, thereby resulting in adsorption of active agent to the crystalline microparticle. Chemical interaction between the microparticle and active agent drives adsorption and results in a monolayer of the active agent on the surface of the microparticle. Once a molecule of active agent is adsorbed, that portion of the microparticle surface is not exposed for further interaction and adsorption of additional active agent at that particular surface point. The resulting monolayer can be either continuous (no gaps between adsorbed active agent molecules over the accessible surface) or non-continuous (gaps of exposed microparticle surface between adsorbed active agent molecules.

Adsorption of Active Agent onto Microparticles

As discussed above, adsorption of the active agent onto the microparticle results in mono-layering (coating) of the active agent onto the microparticle. However, there is more than one mechanism at play in the adsorption of an active agent, such as insulin for example, to crystalline microparticles:

The monolayer of an active agent, such as insulin, that coats the microparticle is one stage of the loading process of insulin onto the microparticle but is not necessarily the end result in the loading process as both monomeric and multimeric layers can be formed based on the energetics of the system.

Under conditions of permissive solubility, such as low insulin concentration and/or low pH (substantially below pH 5.0), attractive forces between insulin and the FDKP particle surface are much greater than the self-associative forces for insulin. Thus coating of insulin onto the microparticle occurs in a monolayer manner and saturation is observed without aggregation or multilayering onto the microparticle surface (see Example 6). As solubility approaches saturation, due to high insulin concentration and/or pH close to 5.0 (a solubility minimum for wild-type insulin), insulin self-association becomes more energetically favorable. Thus coating can proceed past the point of a saturated monolayer and further layers of insulin can be added to the particle. Two forms of self-association can be recognized: multimerization and aggregation. Multimerization is characterized by specific intermolecular interactions and fixed stoichiometry. Aggregation is characterized by unspecific intermolecular interactions and undefined stoichiometry. Speaking generally, multimeric active agents can be adsorbed in the multimeric state, or disassociated into monomers, or lower order multimers, and adsorbed to the surface in that state. In either case aggregation can mediate layering of the active agent onto the microparticle. According to the inventors current understanding, under the general conditions used in the examples of the present disclosure (such as dissolution of insulin in acetic acid) deposition of additional layers of insulin proceed as aggregation of non-hexameric insulin.

Method for Coating Microparticles

The procedure for coating crystalline microparticles, such as preformed crystalline microparticles, with active agents is described generally as follows: crystalline microparticles previously formed by precipitation, or another method, are suspended in liquid medium, such as water; and the medium is adjusted to alter the particles' surface either before or after addition of active agent. At this point the active agent will adsorb to the microparticle surface and after an interval of time (for example <1, 1, 2, 3, 4, 5, 6, 7, 8, 9, or 10 minutes; preferably from <1 to at least 5 minutes) the loading process will be complete. The liquid medium may be removed by any means including filtration, centrifugation, lyophilization or spray-drying or replaced by media exchange. Adsorption may be confirmed by either of two experimental approaches: 1) demonstrating the absence of significant amounts of active agent in a filtrate or supernatant and/or 2) demonstrating presence of the active agent in the solid phase while showing that active agent does not precipitate when taken through the same procedure in the absence of the microparticles.

Manipulating Microparticle Surface Properties

As disclosed elsewhere herein, the surface properties of the microparticle can be manipulated by various means. The microparticle surface properties that can be manipulated include, but are not limited to, electrostatic, hydrophobic, and hydrogen bonding properties. In various embodiments these manipulations are carried out in the absence or presence of the active agent, or before or after the microparticles and the active agent are mixed together. When the manipulation takes place in the presence of the active agent, for example by altering solution condition, there can also be effects on the active agent that will modify its affinity for the surface. Thus in some embodiments of the present invention, coating of the microparticle can involve manipulation of surface properties and modification of properties of the active agent. Methods directed to the latter are disclosed in co-pending U.S. patent application Ser. No. 11/532,065 entitled METHOD OF DRUG FORMULATION BASED ON INCREASING THE AFFINITY OF ACTIVE AGENTS FOR CRYSTALLINE MICROPARTICLE SURFACES filed on date even with the instant application and which is incorporated herein by reference in its entirety.

Electrostatic interactions are attractions between opposite charges or repulsions between like charges that grow stronger as the charges come closer to each other. Electrostatic interactions constitute a key component in understanding interactions between charged bodies in ionic solutions. For example, the stability of colloidal particles dispersed in a solvent can be explained by considering the competition between repulsive electrostatic interactions and the attractive van der Waals interactions. Also, the chemical functionality (for example, but not limited to COOH, NH, etc.) of the microparticle surface can be utilized as the counter ion to an ionized active agent such that the active agent/particle composite comprises a salt. Electrostatic interactions are also of importance when considering interaction and adhesion between particles.

Altering the pH of the surrounding solution system can change electrostatic properties of ionizable crystalline microparticles in suspension. As demonstrated in Example 3, changing the pH of the solution changes the ionization of a microparticle such that active agent adsorbs to the microparticle surface. Specifically, Example 4 shows that microparticles composed of FDKP (3,6-bis[N-fumaryl-N-(n-butyl)amino]2,5-diketopiperazine) are ionizable. The microparticles are insoluble in water below pH 3.5 but solubility increases rapidly between pH 3.5 and 5.0, presumably due to the ionization of the carboxyl groups. The FDKP microparticle is partially ionized at pH 5 prior to complete dissolution at higher pH, which can be observed indirectly via ultrasonic spectroscopy. Example 5 demonstrates the controlled coating of protein onto the FDKP microparticle surface. In one embodiment, diketopiperazine microparticles are suspended in an acidic solution, active agent is added to the suspension, and the pH of the solution is raised after the active agent and microparticles are mixed together. The increased pH alters the surface properties of the microparticles to create an environment in which the active agent has a higher affinity for the microparticle than for the solvent.

Alternatively, the pH of the microparticle suspension can be raised immediately prior to addition of active agent to the solution. The surface charge properties of the microparticle are altered by the change in pH such that active agent has a higher affinity for the microparticle than for remaining in solution and is adsorbed to the microparticle surface upon addition.

Examples 6 and 7 demonstrate loading of insulin onto FDKP particles by manipulation of pH conditions. Finally, the saturation of the microparticle by protein adsorption and the formation of a monolayer are described in Example 6.

Other Methods of Manipulating the Surfaces of Microparticles

In addition to electrostatic properties, other properties of a microparticle surface can be exploited to control adsorption of active agent. Microparticles containing compounds with imidazole, pyridine, Schiff bases, ketone, carboxylic acid bioisosteres, amides, or other functional groups that can exist in multiple structures could be manipulated to modify surface properties.

Hydrophobic interactions are associations of non-polar groups with each other in aqueous solutions because of their insolubility in water. Hydrophobic interactions can affect a number of molecular processes including, but not limited to, structure stabilization (be it of single molecules, complexes of two or three molecules, or larger assemblies) and dynamics, and make important contributions to protein-protein and protein-ligand binding processes. These interactions are also known to play a role in early events of protein folding, and are involved in complex assembly and self-assembly phenomena (e.g., formation of membranes).

Hydrophobic interactions can be manipulated by changing the protonation of crystalline microparticles composed of histidine. Protonating the histidine will reduce the nucelophilicity of the crystalline microparticles and impart a positive charge.

Hydrogen bonding interactions are especially strong dipole-dipole forces between molecules; a hydrogen atom in a polar bond (e.g., H—F, H—O or H—N) can experience an attractive force with a neighboring electronegative molecule or ion, which has an unshared pair of electrons (usually an F, O or N atom on another molecule). Hydrogen bonds are responsible for the unique properties of water and are very important in the organization of biological molecules, especially in influencing the structure of proteins and DNA.

In the present invention, the hydrogen bonding properties of the microparticle surface can be controlled by chemical derivatization. Hydrogen bond donors/acceptors can be added chemically to alter the microparticle surface. For example, the hydrogen in an N—H bond can undergo hydrogen bonding to the oxygen in a C=O bond. If the N—H is replaced by an N—$CH_3$, then this particular hydrogen bonding interaction is removed. Likewise, replacement of the C=O group with a C=C group also removes this particular bonding interaction.

Microparticles with surfaces containing ionizable aromatic groups are polar when ionized but hydrophobic in their un-ionized state. Starting with protonated surfaces and manipulating solution conditions to reduce particle surface ionization causes hydrophobic or aromatic active agents to coat the microparticle surface.

Microparticles with ketone surface groups could be manipulated by changing the solution polarity. By reducing solvent polarity (adding low polarity organic solvents to an aqueous solution) the enol-form is made the predominant species at the particle surface. This enol-form is a hydrogen bond donor whereas the keto-form is a hydrogen bond acceptor. The adsorption of nitrogen-containing drugs onto the microparticle surface is promoted in this manner.

Microparticles with surface groups that undergo pH- or temperature-induced isomerization can also be induced to adsorb drug molecules by manipulating solution conditions. In the case of these surfaces, the introduction of a kink in a linear surface group due to isomerization increases the mobility (fluidity) of the groups at the microparticle surface. This allows the surface to form more contacts with the active agent than are possible with an ordered surface. If the additional interactions with the active agent are each favorable, then the net interaction energy becomes favorable and the drug adsorbs to the microparticle surface.

Fluid Medium Removal Techniques

Removal of solvent after controlled coating of the crystalline surfaces with active agent can be achieved by methods including, but not limited to, sedimentation, filtration, or drying. Drying techniques include, but are not limited to, lyophilization and spray-drying. These techniques are known to those skilled in the art. In one embodiment of the present invention, solvent is removed by spray-drying. Methods of spray-drying diketopiperazine microparticles are disclosed in, for example, U.S. Provisional Patent Application No. 60/776,605 filed on Feb. 22, 2006, incorporated by reference herein for all it contains regarding spray-drying diketopiperazine microparticles.

Analysis of Surface Property Modifications

The present invention employs the technique of ultrasonic spectroscopy to analyze the changes in the surface properties of crystalline microparticles in a fluid suspension, which promote or enhance adsorption of an active agent to the crystalline microparticle. As disclosed elsewhere herein, such changes involve changing solution conditions (such as pH, temperature, polarity, ionic strength, and co-solvents), by complexation to mono- or multi-valent ions, or by chemical derivatization to alter the surface properties of the microparticle either before or after addition of active agent.

Ultrasonic spectroscopy is an analytical tool known to the skilled artisan. In brevity, ultrasonic spectroscopy employs sound waves. In particular, it uses a high frequency acoustical wave which probes intermolecular forces in samples/materials. Oscillating compression (and decompression) in the ultrasonic wave causes oscillation of molecular arrangements in the sample, which responds by intermolecular attraction or repulsion.

Traveling through samples, the ultrasonic wave loses its energy (a decrease in amplitude) and changes its velocity. This decrease in amplitude and change in velocity are analyzed as characteristics of the sample. Therefore, propagation of ultrasonic waves is determined by ultrasonic velocity and attenuation.

Ultrasonic velocity is determined by the elasticity and the density of the medium. Solids have the strongest interactions between the molecules followed by liquids and gases and are therefore more rigid compared with liquids and gases. Ultrasonic attenuation is a measure of the energy that ultrasonic waves lose as they traveling through a sample. It characterizes the ultrasonic transparency of the sample and can be seen as a reduction of amplitude of the wave.

Multi-frequency measurement of ultrasonic attenuation in homogeneous systems allows the analysis of fast chemical reactions such as, but not limited to, proton exchange, structural transitions (e.g., isomerization), self-association (e.g., dimerization), aggregation, binding of ligands to macromolecules etc.

EXAMPLES

The following examples are included to demonstrate embodiments of the present invention. It should be appreciated by those of skill in the art that the techniques disclosed in the examples which follow represent techniques discovered by the inventor to function well in the practice of the present invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Procedure for Loading Microparticles with Active Agents

Table 1 below is an example of electrostatically driven coating of an ionizable crystalline microparticle (FDKP microparticles) utilizing pH-controlled adsorption. In these experiments, FDKP microparticle suspensions were prepared at pH 2.0 and 4.5. Protein (growth hormone) was then added to each to give final conditions of 5 mg/mL FDKP particles and 200 μg/mL protein. After mixing, the bulk liquid was removed from suspension by filtration. The material trapped on the filter was then dissolved and collected. The protein concentration in all of the fractions was quantitated by HPLC.

At low pH (2.0), the protein did not adsorb to the particles and all protein was found in the first filtrate. By increasing the pH to 4.5, the surface properties of the particles were changed to have a high affinity for the protein. Under these conditions, the protein bound to the microparticles and was not seen in the filtrate. To determine the amount of protein associated with the microparticles, the protein was recovered when the microparticles were dissolved. The particle-free controls demonstrate that the protein, by itself, was not retained on the filter under the conditions used, i.e., the protein did not self-associate or otherwise aggregate into particles larger than the filter pores.

TABLE 1

Protein concentrations in an adsorption experiment with FDKP microparticles.

| Fraction | pH 2.0 with particles | pH 2.0 no particles | pH 4.5 with particles | pH 4.5 no particles |
|---|---|---|---|---|
| Initial conc. (µg/mL) | 200 | 200 | 200 | 200 |
| Filtrate (unbound protein) | 146 | 181 | 0 | 145 |
| Dissolved Particles | 0 | 0 | 180 | 0 |

Values shown are results from HPLC quantitation of the solutions after filtration Example 2

Controlling FDKP Microparticle Ionization by Manipulating the pH

FDKP is a rod-shaped molecule with a carboxylic acid functional group at each end which is essentially insoluble in water below pH 3.5 when the carboxylic acids are protonated and carry no charge. The solubility of FDKP increases rapidly above pH 3.5 corresponding to ionization of the carboxyl groups. Modeling of FDKP crystals, which form as plates with two large, flat faces and narrow edges, indicates that the rod-like FDKP molecules align perpendicular to the edges of the plates so that the carboxylic acid ends of the molecule are arrayed on the large faces of the plates. On a theoretical basis, the surfaces of FDKP crystals should be partially ionized around pH 5.0, where the solubility is about 1 mg/mL, just below the pH at which a 10 mg/mL suspension of microparticles will dissolve.

The ionization of FDKP crystal surfaces has been observed indirectly with ultrasonic spectroscopy. In FIG. 1, the ultrasonic titration curve of FDKP microparticles and buffer are shown. In this experiment, a solution containing 200 mM HCl was added in small aliquots to a stirred 10 mg/mL suspension of FDKP microparticles in 20 mM ammonium acetate buffer. The initial pH was 4.8. After each addition of HCl, the system was permitted to equilibrate and ultrasonic data was collected.

The decrease in ultrasonic velocity observed with increasing acid concentration (decreasing pH) reflects the protonation of carboxylic acid groups in the system. As the groups were protonated and became uncharged, the water structure around them relaxed and ultrasonic waves were transmitted more slowly (the ultrasonic velocity decreases). Because FDKP microparticles carboxylate surfaces and the carboxylate group in the acetate buffer are chemically very similar, the curves were also similar. The differences, however, were caused by the FDKP microparticles. First, the magnitude of the velocity change with FDKP microparticles was larger. This difference results from protonation of ionized carboxylate groups on the FDKP microparticle surface. The peak in the attenuation curve, which occurs near the point of complete protonation, was shifted to slightly higher acid concentration in the FDKP suspension. Finally, both FDKP parameters continued to change as the pH was reduced from 3.5 to 2.3. These changes reflect additional modifications in the surface properties of the particles that may include ordering of the surface carboxyl groups or other microstructural modifications.

Example 3

Loading Protein onto FDKP Microparticles by pH Manipulation of the Surface Properties The adsorption of proteins onto ionizable microparticle surfaces by pH manipulation can be achieved in two ways. The protein can be added and then the pH adjusted to cause ionization of the surface with concomitant adsorption of protein. This process is reversible. Alternatively the pH of the particle suspension can be adjusted to cause ionization of the surface before the protein is added.

Figure 2:
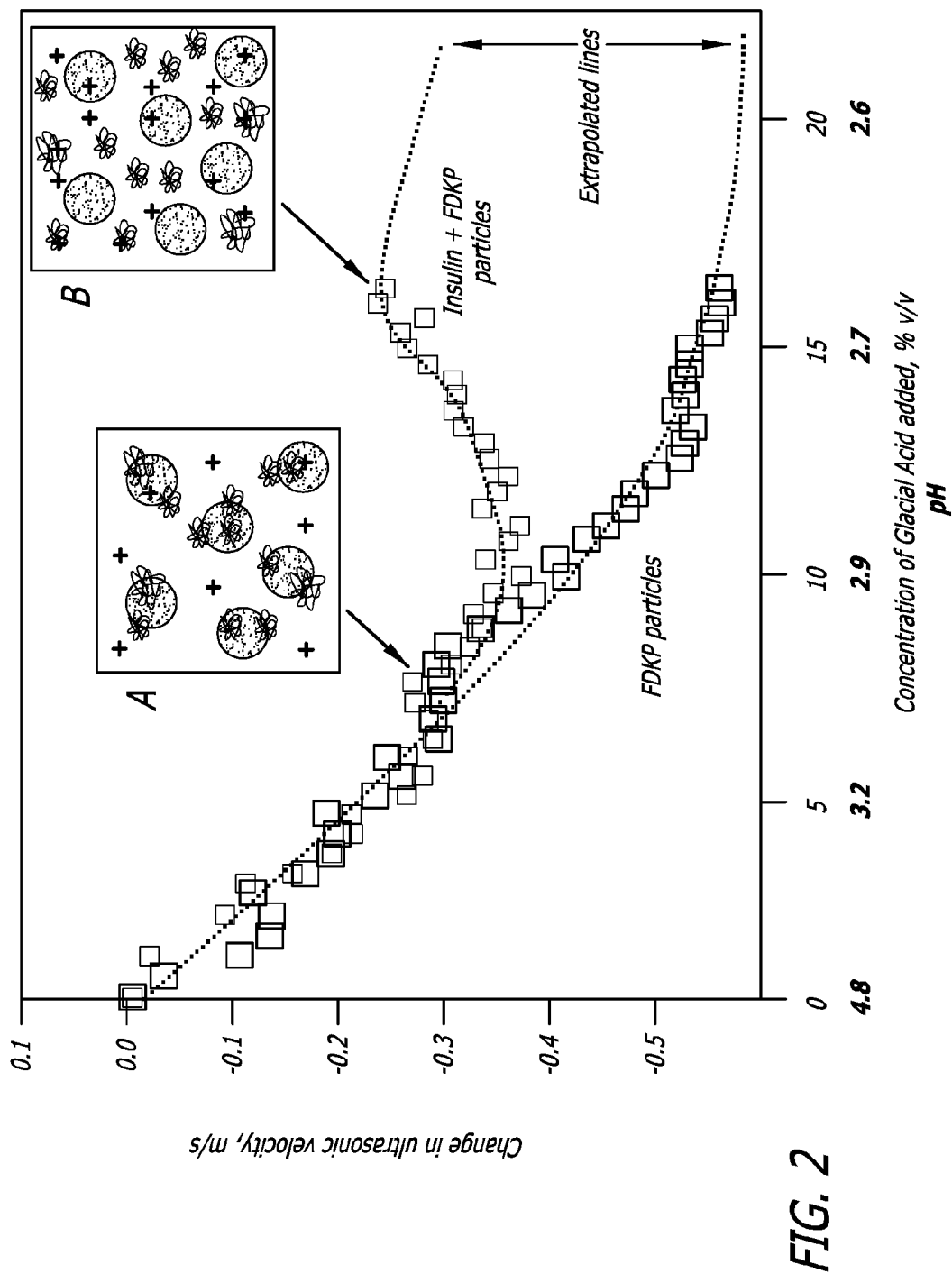

The ultrasonic titration data shown in FIG. 2 indicates the association of protein (insulin) with the FDKP microparticles at pH greater than about 2.9 and reduced interaction at pH below about 2.9.

A suspension of FDKP microparticles was prepared in 20 mM ammonium acetate buffer, pH 4.8, and combined with an insulin stock solution to give 800 µL of suspension with a final concentration of 10 mg/mL FDKP microparticles and insulin concentration of 1 mg/mL. This suspension was introduced into an ultrasonic spectrometer. While stirring gently, glacial acetic acid was gradually added in 5 µL aliquots to lower the pH. At each step in the titration ultrasonic data was collected.

The change in ultrasonic velocity was related (proportional) to the amount of surface area (hydration water) of the particles and/or macromolecules in the sample. FIG. 2 illustrates that above pH of about 2.9 (10% v/v acetic acid added), the velocity curves for microparticles alone (FDKP particles) and microparticles with insulin (FDKP particles+Insulin) coincided. This indicated that the amount of surface area in the system is essentially the same as the surface area of FDKP microparticles alone. The insulin had a negligible contribution because it is very small compared to the microparticles. Below pH 2.9, the FDKP particles and FDKP particles+Insulin curves diverged. Ultrasonic velocity of the FDKP particles+Insulin curve was higher here, which indicated that there was more surface area exposed to water than in the FDKP particles alone sample. This additional surface area was from free insulin in the suspension. As the pH increased from about 2.7 to about 2.9, the insulin surface area was lost by adsorption of insulin to FDKP microparticle surfaces, and the higher intensity of the FDKP microparticles+Insulin curve disappeared as free insulin disappeared from the system.

Figure 3:
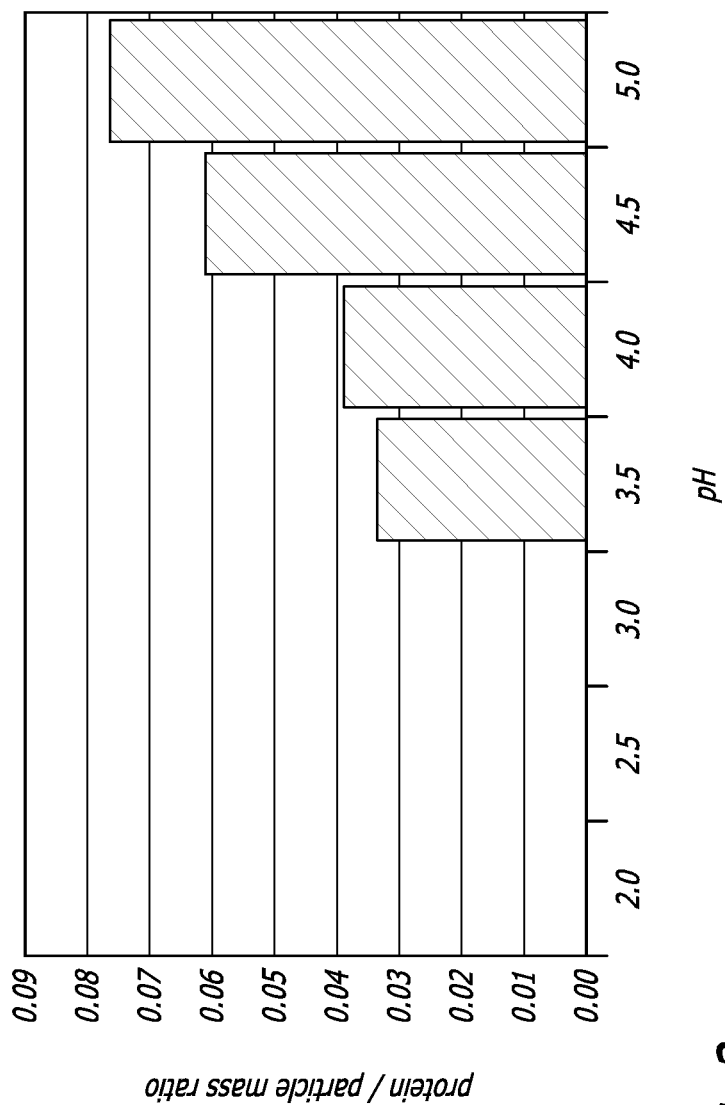

As noted above, the second pH-driven method of coating particles with protein is to suspend particles in a fluid medium and adjust solution conditions to ionize the particle surface. The protein can then be added to the suspension and protein molecules will immediately adsorb. FIG. 3 illustrates the amount of protein (insulin) that was adsorbed upon addition to pH-adjusted suspensions of FDKP microparticles.

FDKP microparticle suspensions were prepared at 5 mg/mL and an excess of protein (2 mg/mL) was added. (An excess of protein, as referred to herein, is that amount over what is believed to be necessary to form a monolayer covering the accessible surface of the FDKP microparticle). After incubation, non-adsorbed protein was removed by filtration. The solids retained on the filter (retentate) were dissolved and the amounts of FDKP microparticles and protein retained on the filter were quantitated by HPLC. The protein/particle mass ratio was determined from this quantitation. Based on the known surface area of these particles and the molecular dimensions of the protein, a continuous monolayer of adsorbed protein was estimated to occur at a mass ratio of about 0.07. On the basis of that estimate it can be seen from this example that a continuous monolayer was formed at pH 5.0 and that non-continuous monolayers formed at pH 3.5 through pH 4.5.

Additionally, different lots of dried active agent-coated FDKP microparticles were suspended in either an acid solution (final pH about 2.0) or water (final pH about 4.5). The different active agents included insulin, growth hormone and insulin aspart (a fast-acting type of insulin), as shown in Table 2. The solvent was filtered from these suspensions and the retained particles were dissolved and collected. The amount of active agent in all of these samples was quantitated by HPLC. The results are shown in Table 2.

For each of the lots, the active agent was released from the particles in the acidic solution. Therefore, by protonating the surfaces of the microcrystals, the active agent desorbs from the crystal surfaces. When the particles were resuspended in water, which does not change the ionization state of the particle surface, the protein remained adsorbed.

TABLE 2

Active agents coated onto FDKP microparticles

|  | Growth Hormone | Insulin | Insulin Aspart |
|---|---|---|---|
| Active Agent Standard solution | 250 | 1103 | 1099 |
| Resuspended in Acidic solution | 240 | 980 | 893 |
| Redissolved after filtering away acidic solution | 0 | 49 | 29 |
| Resuspended in water | 0 | 4 | 0 |
| Redissolved after filtering away water | 191 | 936 | 982 |

Values in the table are integrated peak areas from HPLC quantitation (mAU*sec at 215 nm).

Example 4

Characterization of pH Driven Adsorption of Insulin onto FDKP Microparticles

Figure 4A:
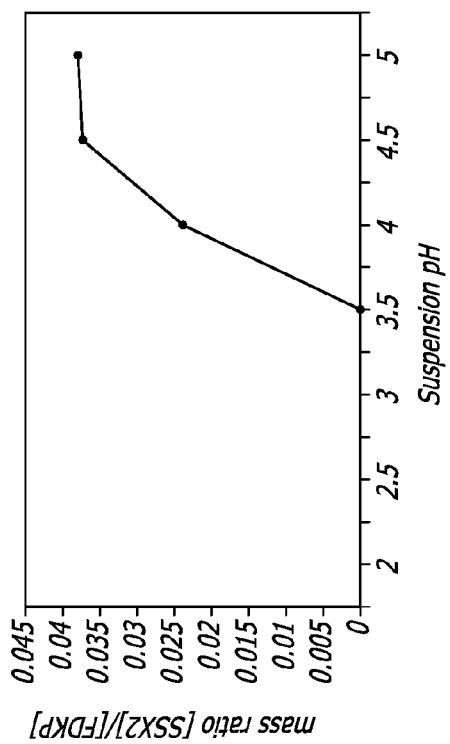
Figure 4B:
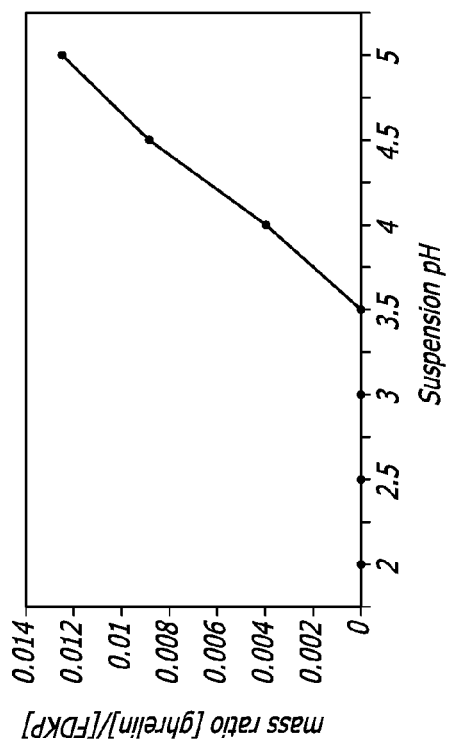
Figure 4C:
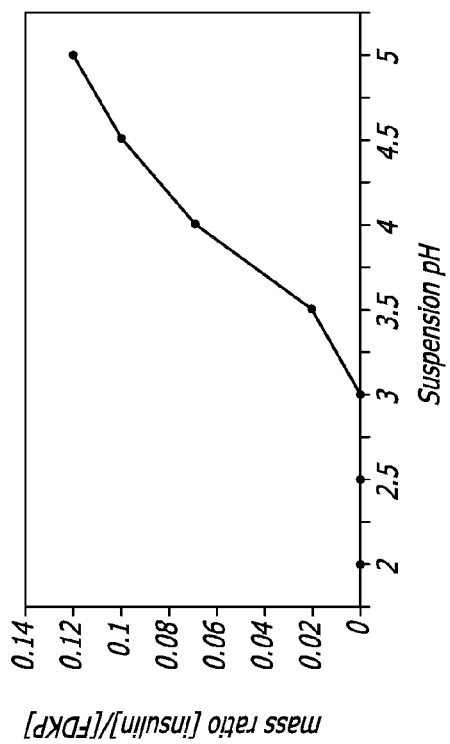
Figure 4D:
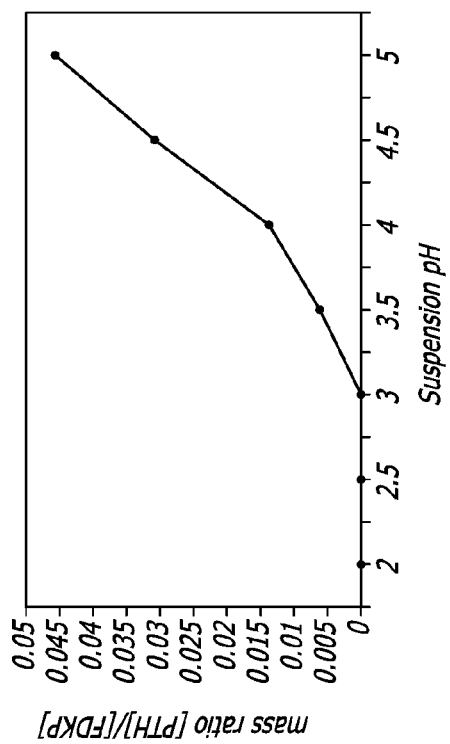

Insulin was adsorbed (loaded) onto FDKP microparticles in a pH-controlled process by mixing an aqueous suspension of FDKP microparticles with an aqueous solution of insulin. To characterize the effect of pH on insulin binding to FDKP microparticles, a 5 mg/mL suspension of FDKP particles at varying pH values was prepared. An excess of dissolved insulin was then added, allowed to adsorb for about 5 minutes, after which the unbound insulin was removed by filtration. The solid particles with adsorbed insulin were recovered from the filter (retentate), dissolved and collected. The amounts of insulin and dissolved FDKP microparticles were quantitated by HPLC. The amount of adsorbed insulin was calculated as a fraction of the total mass of retentate. The pH dependence of insulin adsorption is shown in FIG. 4A; insulin adsorption increased as a function of pH. Similar results were obtained for SSX-2$_{41-49}$ monoclonal antibody, PTH, and ghrelin as illustrated in FIGS. 4B, C, and D respectively.

Figure 5:
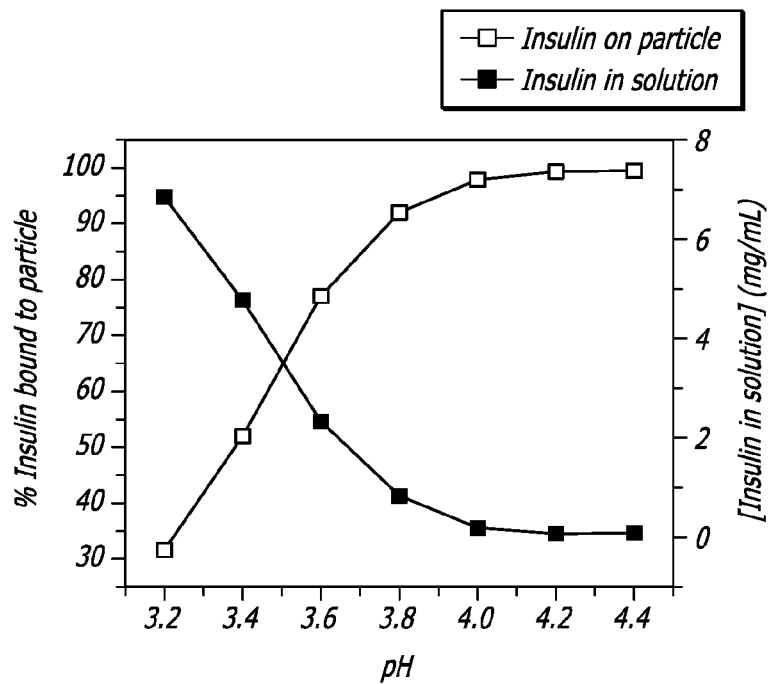

Additionally, FDKP particles were suspended in insulin solutions (10 mg/mL) of different pHs. The mass ratio of FDKP particles to insulin was 10:1. The unbound insulin concentration in the supernatant was determined by HPLC after the supernatant had been separated from the particles by centrifugation. Insulin binding was determined as the difference from the initial insulin concentration. The data reported in FIG. 5 demonstrate that increasing pH resulted in reduced insulin in solution and increased insulin content on the FDKP particles.

Thus, insulin binding to FDKP particles increases with increasing pH from about pH 3.0 up to about pH 5. Preferably, the insulin solution is added at pH 3.6 and under these conditions approximately 75% of the insulin is adsorbed from solution onto the particles. Insulin binding increases to >95% as pH increases to 4.0. Substantially complete binding is achieved at about pH≥4.2, preferably about 4.4. At pH higher than 5.0, the FDKP microparticles begin to dissolve and no longer retain the structure of a crystalline microparticle.

Example 5

Description of Loading FDKP Microparticles with Insulin

In a production scale format (2-5 kg), microparticles of FDKP are formed by acid precipitation with acetic acid and washed. An insulin solution at pH 3.6 is added to the FDKP particle suspension. The insulin stock solution is 10 wt % insulin and 2.5 wt % acetic acid (pH of approximately 3.6). Ammonium hydroxide is used to adjust the pH of the mixture to 4.5. Table 3 indicates the amounts of the various components per kilogram of formulation used to prepare particles containing ~11.4% insulin by weight. Polysorbate 80 can be incorporated during particle formation and can improve the handling characteristics of the final particles. Time is allowed for insulin adsorption onto the FDKP particles and to ensure thorough mixing. The mixture is then added dropwise to liquid nitrogen to flash freeze the suspension. The fluid medium is removed by lyophilization to produce FDKP particle/insulin bulk drug product. Alternatively the mixture is spray-dried. Table 4 indicates the amounts of the various components in the bulk product after removal of the fluid medium.

TABLE 3

Composition of FDKP particles/Insulin Batch Formula

| Component | 11.4% FDKP/Insulin (Grams per kg of formulation) |
|---|---|
| Insulin, USP | 114 g |
| FDKP | 870 g |
| Polysorbate 80, USP* | 34.8 g |
| Strong Ammonia Solution, NF | 572 g |
| Acetic acid (glacial), NF | 3680 g |
| Purified Water, NF | 179000 g |
| Nitrogen, NF | as needed |

TABLE 4

Composition of FDKP particles/Insulin

| Component | 11.4% FDKP/Insulin, process (Quantity per milligram formulation) |
|---|---|
| Insulin, USP | 3.0 IU (0.11 mg) |
| FDKP | 0.87 mg |
| Polysorbate 80, USP* | 0.007 mg |
| Strong Ammonia Solution, NF | Removed during process |
| Acetic acid (glacial), NF | Removed during process |
| Purified Water, NF | 0.012 mg |
| Nitrogen, NF | Removed during process |

In Tables 3 and 4 above, NF denotes—National Formulary
*Polysorbate 80 content is estimated by an HPLC/MS assay.
**The FDKP/Insulin formulation contains about 1.2% residual water after lyophilization. Trace quantities of acetic acid and ammonium hydroxide may also be present.

Example 6

Saturation of Microparticle Surfaces by Protein (Formation of a Continuous Monolayer)

Figure 6:
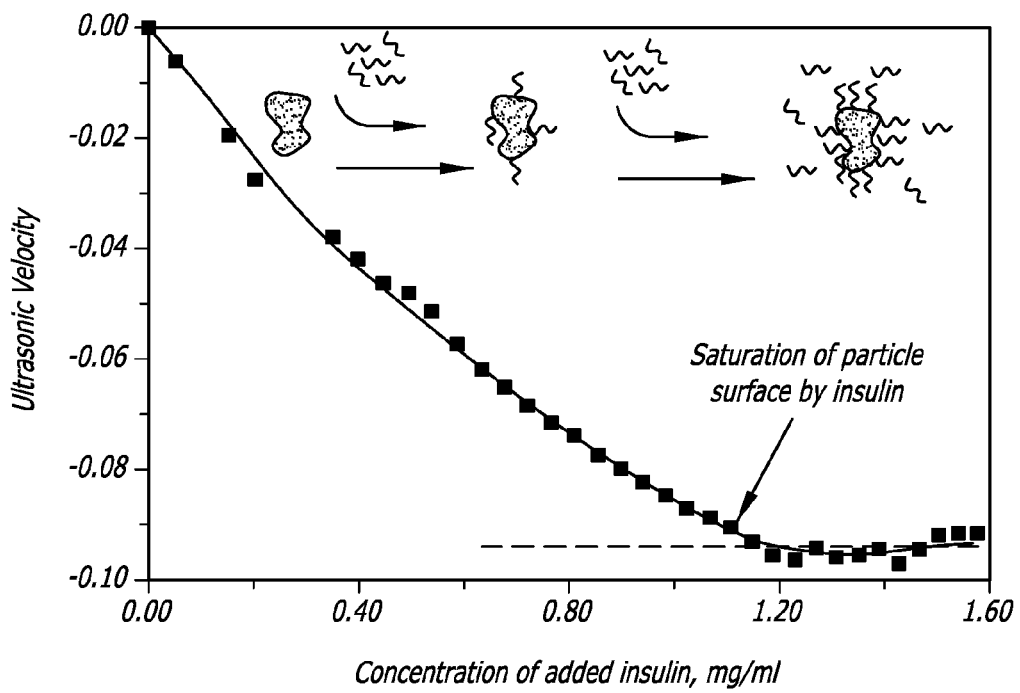

The surface coating of a microparticle with a monolayer should be a saturable process. That is, its accessible surface area and the diameter of the active agent molecule will dictate the capacity of the microparticle surface. FIG. 6 illustrates this saturation.

A suspension of FDKP microparticles was prepared and the pH was adjusted to between pH 3.0 and pH 3.5 at which point the surfaces partially ionize. In this procedure, higher pH could not be used because it would have caused self-association of the active agent, insulin. Small portions of a concentrated insulin solution were added to the stirred suspension. After each addition, the sample was allowed to stabilize and ultrasonic data was collected.

Figure 7A:
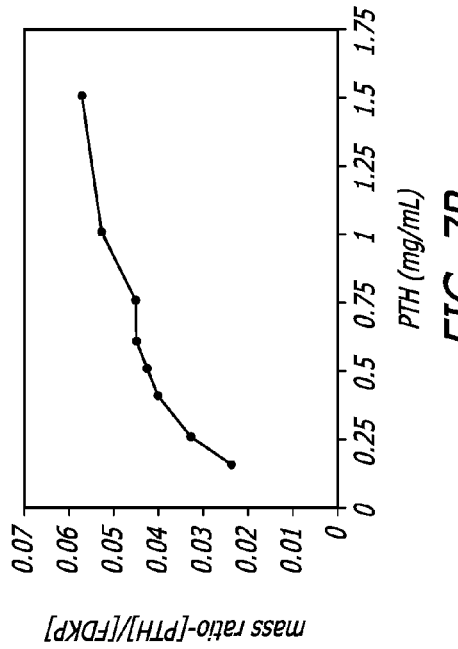
Figure 7B:
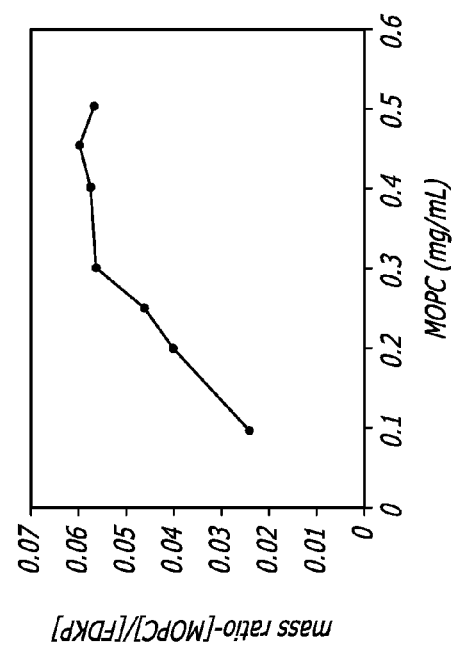
Figure 7C:
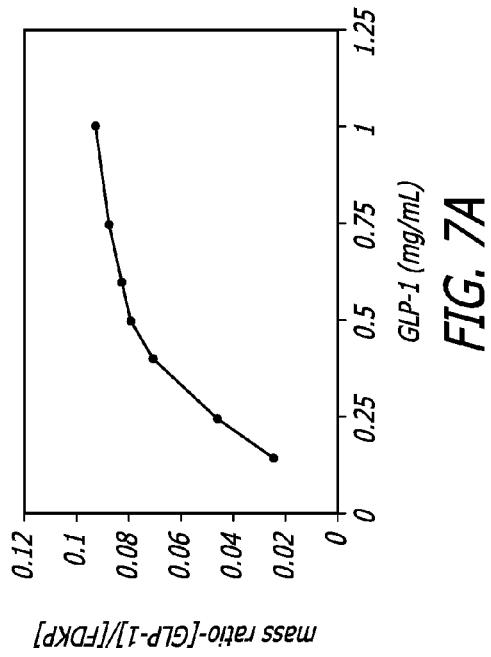
Figure 7D:
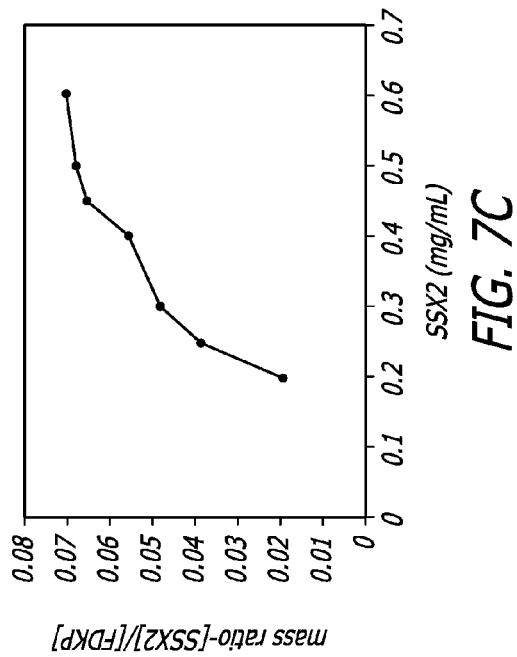

FIG. 6 shows that a reduction in ultrasonic velocity is observed as the protein concentration was increased. This type of change in the ultrasonic velocity is typical for ligand binding in aqueous solutions and indicates adsorption of the active protein to the FDKP microparticle surfaces. The velocity decrease results from the release of hydration water from the FDKP microparticle and protein surfaces. When the hydration water is displaced by adsorption of the active agent, its structure relaxes and produces a net decrease in the ultrasonic velocity through the sample. When all the binding sites on the surface of the FDKP microparticles have been saturated, i.e., a protein monolayer has formed, the curve levels off. Monolayer formation was also demonstrated by the data in FIGS. 7A-7D which showed that the adsorption of various active agents (GLP-1 [FIG. 7A]; PTH [FIG. 7B]; anti-SSX-2$_{41-49}$ monoclonal antibody [FIG. 7C]; and anti-MOPC-21 monoclonal antibody [FIG. 7D]), onto microparticles reached saturation as the concentration of the active agent is increased at a constant concentration of FDKP microparticles (5 mg/mL). These studies were conducted at pH 5.0 where optimal adsorption of the active agent to microparticles is observed. GLP-1 does not self associate at the concentrations used (as disclosed in U.S. Provisional Patent Application No. 60/744,882).

Example 7

Evidence for Electrostatic Interaction Mechanism

Evidence for an electrostatic mechanism of interaction is the ability to interfere with adsorption by weakening electrostatic interactions. This is demonstrated by adding salt to the ionized-particle/active agent system. FIGS. 8A-8D illustrate that increasing ionic strength in an active agent-FDKP microparticle system reduced the adsorption of the active agent onto the microparticle.

A series of samples were prepared at pH 5.0 where adsorption of the active agent onto FDKP microparticle surfaces is strong. Each sample contained a different quantity of salt (sodium chloride), as indicated under each bar in FIGS. 8A-8D (units are mM). The active agent was mixed into the suspension to give a final concentration of 5 mg/mL FDKP microparticles and 0.75 mg/mL insulin (an excess; FIG. 8A). After a brief incubation, unbound active agent was removed by filtration and the particles with adsorbed active agent were redissolved. The amount of active agent and particle recovered was quantitated by HPLC, and expressed as a mass ratio (% loading). FIGS. 8A-8D illustrate that increasing ionic strength in a active agent-FDKP microparticle system reduced the extent of adsorption of active agents including anti-SSX-2$_{41-49}$ monoclonal antibody (0.2 mg/mL; FIG. 8B), ghrelin (0.1 mg/mL; FIG. 8C) and PTH (0.25 mg/mL; FIG. 8D) in the presence of 5 mg/mL FDKP microparticles.

FIG. 8 shows an inverse correlation between the measured adsorption and the salt concentration in the loading suspension. This can be interpreted as evidence that the salt competed with the active agent for interaction with the particle surface. As the salt concentration was increased, it competed strongly and effectively for surface binding sites, and essentially displaced the active agent from the particle surfaces. It is also speculated, that decrease binding of the active agent to microparticle may be attributable to Debye shielding.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and an and the and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term or in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed:

1. A microparticle comprising a fumaryl diketopiperazine (FDKP) core and an active agent coating;
   wherein at least a portion of the active agent is bound to a surface of the FDKP core, and wherein the surface of the FDKP core to which the active agent is bound contains a plurality of carboxylic acid groups, part of which are ionized;
   wherein the plurality of carboxylic acid groups are ionized in an amount that is equivalent to the amount of ionized carboxylic acid groups that would be present on the surface if the FDKP core were dispersed in an aqueous solution having a pH of about 4 to about 5.

2. The microparticle of claim 1, wherein the plurality of carboxylic acid groups are ionized in an amount that is equivalent to the amount of ionized carboxylic acid groups that would be present on the surface if the FDKP core were dispersed in an aqueous solution having a pH of about 4.4 to about 5.

3. The microparticle of claim 1, comprising about 9% to about 12% active agent by weight.

4. The microparticle of claim 1, wherein the core microparticle further comprises polysorbate 80.

5. The microparticle of claim 1, comprising at least 0.7% polysorbate 80 by weight.

6. The microparticle of claim 5, comprising between 0.7% and 3.5% polysorbate 80 by weight.

7. The microparticle of claim 1, wherein the active agent coating is predominantly a monolayer.

8. The microparticle of claim 1, wherein at least a portion of the active agent is electrostatically bound to the FDKP core.

9. The microparticle of claim 8, wherein a majority of the active agent coating is bound to the FDKP core.

10. The microparticle of claim 9, wherein the active agent coating is bound so that a majority of the active agent coating will remain on the surface of the FDKP core when the microparticle is dispersed in water.

11. The microparticle of claim 1, wherein the active agent coating is about 11.4% of the total weight of microparticle.

12. The microparticle of claim 1,
    wherein the pharmaceutical microparticle is prepared by a process comprising providing a dispersion of preformed FDKP microparticles in an aqueous solution comprising an active agent, the solution having a pH of about 4.2 to about 5 to adjust the surface charge density of the preformed FDKP microparticles.

13. The microparticle of claim 12, comprising about 10% to about 12% active agent by weight.

14. The microparticle of claim 12, wherein the FDKP core further comprises polysorbate 80.

15. The microparticle of claim 1, wherein the active agent comprises at least one of a peptide, polypeptide, or a protein.

16. The microparticle of claim 1, wherein the active agent comprises at least one of insulin, parathyroid hormone, growth hormone, ghrelin, GLP-1, anti-SSZ2$_{41\text{-}49}$ monoclonal antibody, or anti-MOPC-21 monoclonal antibody.

17. The microparticle of claim 1, wherein the active agent comprises at least one of insulin, an insulin analog, growth hormone, parathyroid hormone, ghrelin, granulocyte macrophage colony stimulating factor (GM-CSF), glucagon-like peptide 1 (GLP-1), Texas Red, alkynes, cyclosporins, clopiogrel and PPACK (D-phenylalanyl-L-prolyl-L-arginine chloromethyl ketone), or antibodies and fragments thereof.

18. The microparticle of claim 17, wherein the antibodies or fragments thereof include humanized or chimeric antibodies.

19. The microparticle of claim 18, wherein the humanized or chimeric antibodies are selected from F(ab); F(ab)$_2$; single-chain antibody alone or fused to other polypeptides; therapeutic or diagnostic monoclonal antibodies to cancer antigens, cytokines, infectious agents, inflammatory mediators, hormones, and cell surface antigens.

20. The microparticle of claim 19, wherein the antibodies to tumor antigens are selected from anti-SSX-$2_{41-49}$, anti-NY-ESO-1, anti-PRAME, anti-PSMA, anti-Melan-A, anti-tyrosinase, and anti-MOPC-21.

* * * * *